United States Patent
Sugiyama et al.

(10) Patent No.: US 10,815,288 B2
(45) Date of Patent: Oct. 27, 2020

(54) ANTIGEN-SPECIFIC HELPER T-CELL RECEPTOR GENES

(71) Applicant: International Institute of Cancer Immunology, Inc., Suita-shi, Osaka (JP)

(72) Inventors: Haruo Sugiyama, Minoo (JP); Fumihiro Fujiki, Hyogo (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 0 days.

(21) Appl. No.: 14/427,465

(22) PCT Filed: Sep. 12, 2013

(86) PCT No.: PCT/JP2013/074748
§ 371 (c)(1),
(2) Date: Mar. 11, 2015

(87) PCT Pub. No.: WO2014/042226
PCT Pub. Date: Mar. 20, 2014

(65) Prior Publication Data
US 2016/0009781 A1 Jan. 14, 2016

(30) Foreign Application Priority Data
Sep. 12, 2012 (JP) .................................. 2012-200480

(51) Int. Cl.
| | | |
|---|---|---|
| *A61K 48/00* | (2006.01) | |
| *C07K 14/725* | (2006.01) | |
| *C12N 5/0783* | (2010.01) | |
| *A61K 35/17* | (2015.01) | |
| *C12Q 1/6886* | (2018.01) | |
| *C07K 16/28* | (2006.01) | |
| *C12Q 1/6881* | (2018.01) | |
| *G01N 33/569* | (2006.01) | |
| *A61K 38/00* | (2006.01) | |

(52) U.S. Cl.
CPC .......... *C07K 14/7051* (2013.01); *A61K 35/17* (2013.01); *C07K 16/28* (2013.01); *C12N 5/0636* (2013.01); *C12Q 1/6881* (2013.01); *C12Q 1/6886* (2013.01); *G01N 33/56972* (2013.01); *A61K 38/00* (2013.01); *C12Q 2600/158* (2013.01); *G01N 2333/4703* (2013.01); *G01N 2333/70514* (2013.01)

(58) Field of Classification Search
None
See application file for complete search history.

(56) References Cited

U.S. PATENT DOCUMENTS

| | | | |
|---|---|---|---|
| 7,420,034 B2 | 9/2008 | Sugiyama et al. | |
| 7,622,119 B2 | 11/2009 | Sugiyama | |
| 7,666,985 B2 | 2/2010 | Sugiyama et al. | |
| 8,388,975 B2 | 3/2013 | Sugiyama | |
| 8,653,038 B2 | 2/2014 | Sugiyama | |
| 8,759,483 B2 | 6/2014 | Sugiyama | |
| 8,778,350 B2 | 7/2014 | Sugiyama | |
| 8,933,038 B2 | 1/2015 | Sugiyama | |
| 8,945,578 B2 | 2/2015 | Sugiyama | |
| 8,968,745 B2 | 3/2015 | Sugiyama | |
| 9,205,111 B2 | 12/2015 | Nishimura et al. | |
| 2004/0097703 A1 | 5/2004 | Sugiyama | |
| 2007/0191496 A1 | 8/2007 | Stauss et al. | |
| 2008/0019948 A1 | 1/2008 | Nishimura et al. | |
| 2008/0070835 A1* | 3/2008 | Sugiyama ........ | A61K 39/0011 424/192.1 |
| 2009/0325886 A1 | 12/2009 | Sugiyama | |
| 2010/0190163 A1 | 7/2010 | Sugiyama | |
| 2010/0247556 A1 | 9/2010 | Sugiyama | |
| 2011/0274675 A1 | 11/2011 | Stauss et al. | |
| 2013/0196427 A1 | 8/2013 | Sugiyama | |
| 2013/0243800 A1 | 9/2013 | Sugiyama | |
| 2013/0266958 A1 | 10/2013 | Sugiyama et al. | |
| 2014/0134200 A1 | 5/2014 | Sugiyama | |
| 2015/0147302 A1 | 5/2015 | Stauss et al. | |

FOREIGN PATENT DOCUMENTS

| | | |
|---|---|---|
| JP | 2008-263950 | 11/2008 |
| JP | 2009-011236 | 1/2009 |
| WO | WO 02/079253 A1 | 10/2002 |

(Continued)

OTHER PUBLICATIONS

Genbank accession No. AYN23233, entry date Mar. 3, 2011, Hiroaki et al. WO2010150819.*
Farkona et al. BMC medicine, 2016, vol. 14:73, pp. 1-18.*
Haber, D.A., et al., An Internal Deletion within an 11p13 Zinc Finger Gene Contributes to the Development of Wilms' Tumor, Cell, Jun. 29, 1990, 61(7), pp. 1257-1269.
Call, K.M., et al., Isolation and Characterization of a Zinc Finger Polypeptide Gene at the Human Chromosome 11 Wilms' Tumor Locus, Cell, Feb. 9, 1990. 60(3), pp. 509-520.

(Continued)

*Primary Examiner* — Celine X Qian

(74) *Attorney, Agent, or Firm* — Finnegan, Henderson, Farabow, Garrett & Dunner, LLP

(57) ABSTRACT

The present invention pertains to polynucleotides that encode CDR3 in TCR-[alpha] and TCR-[beta] chain genes of CD4+ helper T-cells that are specific to WT1 helper peptides having an amino acid sequence represented by SEQ ID NO: 123. The present invention further pertains to the peptides encoded by said polynucleotides. The present invention further pertains to CD4+ T cells into which TCR genes that contain said polynucleotides have been introduced, the induction of WT1-specific cytotoxic T-lymphocytes (CTLs) using the CD4+ T-cells, the treatment of cancer, etc.

1 Claim, 18 Drawing Sheets

Specification includes a Sequence Listing.

(56) References Cited

FOREIGN PATENT DOCUMENTS

| WO | WO 03/106682 A1 | 12/2003 |
|---|---|---|
| WO | WO 2005/045027 A1 | 5/2005 |
| WO | WO 2005/056595 A2 | 6/2005 |
| WO | WO 2005/095598 A1 | 10/2005 |
| WO | WO 2007/097358 A1 | 8/2007 |
| WO | WO 2008/081701 A1 | 7/2008 |
| WO | WO 2008/105462 A1 | 9/2008 |
| WO | WO 2008/108257 A1 | 9/2008 |
| WO | WO 2011/008502 A2 | 1/2011 |
| WO | WO 2011/039508 A2 | 4/2011 |
| WO | WO 2012/046730 A1 | 4/2012 |

OTHER PUBLICATIONS

Menke, A.L., et al., The Wilms' Tumor 1 Gene: Oncogene or Tumor Suppressor Gene? Int Rev Cytol, 1998, 181, pp. 151-212.

Yamagami, T. et al., Growth Inhibition of Human Leukemic Cells by WT1 (Wilms Tumor Gene) Antisense Oligodeoxynucleotides: Implications for the Involvement of WT1 in Leukemogenesis, Blood, Apr. 1, 1996, 87(7), pp. 2878-2884.

Inoue, K., et al., Wilms' Tumor Gene (WT2) Completes With Differentiation-Inducing Signal in Hematopoietic Progenitor Cells, Blood, Apr. 15, 1998, 91(8), pp. 2969-2976.

Tsuboi, A., et al, Constitutive expression of the Wilms' tumor gene WT1 inhibits the differentiation of myeloid progenitor cells but promotes their proliferation in response to granulocyte-colony stimulating factor (G-CSF), Leuk Res., May 23, 1999, 23(5), pp. 49-505.

Oka, Y, et al., Human cytotoxic T-lymphocyte responses specific for peptides of the wild-type Wilms' tumor gene (WT1) product, Immunogenetics, Feb. 2000, 51(2), pp. 99-107.

Gao. F.G., et al.. Anti gen-specific $CD4^+$ T-Cell Help Is Required to Activate a Memory $CD8^+$ T Cell to a Fully Functional Tumor Killer Cell, Cancer Res. Nov. 15, 2002, 62(22), pp. 6438-6441.

Zeng, G., MHC Class II-Restricted Tumor Antigens Recognized by $CD4^+$ T Cells: New Strategies or Cancer Vaccine Design, J Immunother, May 2001, 24(3), pp. 195-204.

Knights, A.J., et al., Prediction of an HLA-DR-binding peptide derived from Wilms' tumour 1 protein and demonstration of in in vitro immunogenicity of WT1 (124-138)-pulsed dendritic cells generated according to an optimized protocol, Cancer Immunol Immunother, Jul. 2002, 51(5), pp. 271-281.

Chamoto, K., et al., Potentiation of Tumor Eradication by Adoptive Immunotherapy with T-cell Receptor Gene-Transduced T-Helper Type 1 Cells, Cancer Res. Jan. 1, 2004, 64(1) pp. 386-390.

Zarour H.M. et al., NY-ESO-1 119-143 Is a Promiscuous Major Histocompatibility Complex Class II T-Helper Epitope Recognized by Th1- and Th2-Type Tumor-reactive CD4+ t Cells, Cancer Res. Jan. 1, 2002, 62(1), pp. 213-218.

Pfizenmaier, K. et al., T-T cell interactions during in vitro cytotoxic lymphocyte responses III. Antigen-specific T helper cells release nonspecific mediator(s) able to help induction of H-2-restricted cytotoxic T lymphocyte responses across cell-impermeable membranes, Eur.J. Immunol., Aug. 1980. 10(8), pp. 577-582.

Pilch, H., et al., Antigen-Driven T-Cell Selection in Patients with Cervical Cancer as Evidenced by T-Cell Receptor Analysis and Recognition of Autologous Tumor, Clin. Diagn. Lab Immunol., Mar. 2002, 9(2), pp. 267-278.

Straten, P.T., et al., T-cell clonotypes in cancer, J. Transl. Med., 2004, 2 (11), pp. 1-10.

International Preliminary Report on Patentability for International Application No. PCT/JP2013/074748 dated Mar. 26, 2015 from the International Bureau of WIPO.

Database EMBL [Online], Jul. 18, 1996, retrieved from EBI accession No. EM_STD: U55105.

Database Geneseq [Online], Jan. 5, 2012, retrieved from EBI accession No. GSP: AZP60910.

Partial Supplementary European Search Report for corresponding EP Application No. 13837129.9 dated Mar. 31, 2016.

Vollmer, Joerg et al., "Dominance of the BV17 element in nickel-specific human T cell receptors relates to severity of contact sensitivity," European Journal of Immunology, vol. 27, No. 8, 1997, pp. 1865-1874.

Database EMBL [Online], Oct. 14, 1994, retrieved from EBI accession No. EM_STD: U14043.

Database EMBL [Online], Sep. 26, 2000, retrieved from EBI accession No. EM_STD: AY006317.

Extended European Search Report dated Sep. 9, 2016, issued in corresponding EP Patent Application No. 13637129.9.

Office Action dated Jan. 22, 2019 by the Japanese Patent Office in Japanese Application No. 2014-535597 (5 pages).

Fujiki, Fumihiro et al., "A WT1 Protein-Derived, Naturally Processed 16-mer Peptide, $WT1_{332}$, is a Promiscuous Helper Peptide for Induction of WT1-specific Th1-type CD4+ T Cells," Microbiol Immunol 2008, 52:591-600.

Fujiki, Fumihiro et al., "A Clear Correlation Between WT1-specific Th Response and Clinical Response in WT1 CTL Epitope Vaccination," Anticancer Research 30: 2247-2254 (2010).

Communication Pursuant to Article 94(3) EPC issued in corresponding EP Application No. 13837129.9 dated Aug. 6, 2020.

Communication Pursuant to Article 94(3) EPC issued in corresponding EP Application No. 18215510.1 dated Sep. 2, 2020.

* cited by examiner

SEQUENCE LISTING

```
<160> NUMBER OF SEQ ID NOS: 125

<210> SEQ ID NO 1
<211> LENGTH: 42
<212> TYPE: DNA
<213> ORGANISM: Homo sapiens

<400> SEQUENCE: 1
tgtgctgtgg gtagctctag caacacaggc aaactaatct tt                    42

<210> SEQ ID NO 2
<211> LENGTH: 51
<212> TYPE: DNA
<213> ORGANISM: Homo sapiens

<400> SEQUENCE: 2
tgcgccagca gccaagacgc tatagggaca ggggttttga aactgttttt t          51

<210> SEQ ID NO 3
<211> LENGTH: 36
<212> TYPE: DNA
<213> ORGANISM: Homo sapiens

<400> SEQUENCE: 3
tgtgctgctt cgtttggaaa tgagaaatta accttt                           36

<210> SEQ ID NO 4
<211> LENGTH: 45
<212> TYPE: DNA
<213> ORGANISM: Homo sapiens

<400> SEQUENCE: 4
tgtgccagca gcgcctcgga cagggagacg tatggctaca ccttc                 45

<210> SEQ ID NO 5
<211> LENGTH: 42
<212> TYPE: DNA
<213> ORGANISM: Homo sapiens

<400> SEQUENCE: 5
tgtgcggaag ctggtggtac tagctatgga aagctgacat tt                    42
```

```
<210> SEQ ID NO 6
<211> LENGTH: 42
<212> TYPE: DNA
<213> ORGANISM: Homo sapiens

<400> SEQUENCE: 6
tgtgccagct gtcggactag ctcctacaat gagcagttct tc              42

<210> SEQ ID NO 7
<211> LENGTH: 39
<212> TYPE: DNA
<213> ORGANISM: Homo sapiens

<400> SEQUENCE: 7
tgtgccagca gcttcactag cacagatacg cagtatttt                  39

<210> SEQ ID NO 8
<211> LENGTH: 39
<212> TYPE: DNA
<213> ORGANISM: Homo sapiens

<400> SEQUENCE: 8
tgtgctgccc cctctggcaa cacaggcaaa ctaatctttt                 39

<210> SEQ ID NO 9
<211> LENGTH: 42
<212> TYPE: DNA
<213> ORGANISM: Homo sapiens

<400> SEQUENCE: 9
tgtgccagca caatagcggg gggggaggat acgcagtatt tt              42

<210> SEQ ID NO 10
<211> LENGTH: 30
<212> TYPE: DNA
<213> ORGANISM: Homo sapiens

<400> SEQUENCE: 10
tgtgccgtga ccggtaacca gttctatttt                            30

<210> SEQ ID NO 11
<211> LENGTH: 42
<212> TYPE: DNA
<213> ORGANISM: Homo sapiens

<400> SEQUENCE: 11
tgtgcagcaa gtgtgggatc agatggccag aagctgctct tt              42

<210> SEQ ID NO 12
<211> LENGTH: 45
<212> TYPE: DNA
<213> ORGANISM: Homo sapiens

<400> SEQUENCE: 12
tgtgccagca gtttcttccg cagggacggg gagacccagt acttc            45

<210> SEQ ID NO 13
<211> LENGTH: 54
<212> TYPE: DNA
<213> ORGANISM: Homo sapiens

<400> SEQUENCE: 13
tgtgttgtga gtgacaatcg tgctggtggt actagctatg gaaagctgac attt  54
```

```
<210> SEQ ID NO 14
<211> LENGTH: 42
<212> TYPE: DNA
<213> ORGANISM: Homo sapiens

<400> SEQUENCE: 14
tgtgcagaga atagtggagg tagcaactat aaactgacat tt                    42

<210> SEQ ID NO 15
<211> LENGTH: 42
<212> TYPE: DNA
<213> ORGANISM: Homo sapiens

<400> SEQUENCE: 15
tgtgccagca cggcaggggc gagcgatcag ccccagcatt tt                    42

<210> SEQ ID NO 16
<211> LENGTH: 39
<212> TYPE: DNA
<213> ORGANISM: Homo sapiens

<400> SEQUENCE: 16
tgtgcctccc ggaataatgc aggcaacatg ctcaccttt                        39

<210> SEQ ID NO 17
<211> LENGTH: 48
<212> TYPE: DNA
<213> ORGANISM: Homo sapiens

<400> SEQUENCE: 17
tgtgccagca gttactcgaa ccgcgggtat aattcacccc tccacttt              48

<210> SEQ ID NO 18
<211> LENGTH: 36
<212> TYPE: DNA
<213> ORGANISM: Homo sapiens

<400> SEQUENCE: 18
tgtgctacgg acgagggaaa tgagaaatta accttt                           36

<210> SEQ ID NO 19
<211> LENGTH: 42
<212> TYPE: DNA
<213> ORGANISM: Homo sapiens

<400> SEQUENCE: 19
tgtgccagca gcttagtcgg cgtctcctac gagcagtact tc                    42

<210> SEQ ID NO 20
<211> LENGTH: 39
<212> TYPE: DNA
<213> ORGANISM: Homo sapiens

<400> SEQUENCE: 20
tgtgcagagg ctgtctatgg gaacaacaga ctcgctttt                        39

<210> SEQ ID NO 21
<211> LENGTH: 42
<212> TYPE: DNA
<213> ORGANISM: Homo sapiens

<400> SEQUENCE: 21
```
tgtgccagtg acaggacagg tagcgacact gaagctttct tt        42

<210> SEQ ID NO 22
<211> LENGTH: 36
<212> TYPE: DNA
<213> ORGANISM: Homo sapiens

<400> SEQUENCE: 22
tgtgctgtgg ataactatgg tcagaatttt gtcttt              36

<210> SEQ ID NO 23
<211> LENGTH: 45
<212> TYPE: DNA
<213> ORGANISM: Homo sapiens

<400> SEQUENCE: 23
tgcatcgtca agggtggggg atacaacttc aacaaatttt acttt     45

<210> SEQ ID NO 24
<211> LENGTH: 42
<212> TYPE: DNA
<213> ORGANISM: Homo sapiens

<400> SEQUENCE: 24
tgtgccagta gtatgggggt cggggacact gaagctttct tt        42

<210> SEQ ID NO 25
<211> LENGTH: 39
<212> TYPE: DNA
<213> ORGANISM: Homo sapiens

<400> SEQUENCE: 25
tgtgctacgg acggggggg agcccagaag ctggtatttt            39

<210> SEQ ID NO 26
<211> LENGTH: 42
<212> TYPE: DNA
<213> ORGANISM: Homo sapiens

<400> SEQUENCE: 26
tgtgccagca ccggacaggg gatcggaaac accatatatt tt        42

<210> SEQ ID NO 27
<211> LENGTH: 42
<212> TYPE: DNA
<213> ORGANISM: Homo sapiens

<400> SEQUENCE: 27
tgtgctctat atagtggagg tagcaactat aaactgacat tt        42

<210> SEQ ID NO 28
<211> LENGTH: 36
<212> TYPE: DNA
<213> ORGANISM: Homo sapiens

<400> SEQUENCE: 28
tgtgcaatga gtcttaacga ctacaagctc agcttt              36

<210> SEQ ID NO 29
<211> LENGTH: 36
<212> TYPE: DNA
<213> ORGANISM: Homo sapiens

<400> SEQUENCE: 29
tgcagcgcaa acgacgggac agatacgcag tatttt 36

<210> SEQ ID NO 30
<211> LENGTH: 36
<212> TYPE: DNA
<213> ORGANISM: Homo sapiens

<400> SEQUENCE: 30
tgtgcagccc caggggggaga tgacaagatc atcttt 36

<210> SEQ ID NO 31
<211> LENGTH: 42
<212> TYPE: DNA
<213> ORGANISM: Homo sapiens

<400> SEQUENCE: 31
tgtgctctag cccaaactga cagctggggg aaattccagt tt 42

<210> SEQ ID NO 32
<211> LENGTH: 42
<212> TYPE: DNA
<213> ORGANISM: Homo sapiens

<400> SEQUENCE: 32
tgtgccagca gcttaccagg acaggcctac gagcagtact tc 42

<210> SEQ ID NO 33
<211> LENGTH: 51
<212> TYPE: DNA
<213> ORGANISM: Homo sapiens

<400> SEQUENCE: 33
tgtgctgtga gtgatcaaaa actcacggga ggaggaaaca aactcacctt t 51

<210> SEQ ID NO 34
<211> LENGTH: 51
<212> TYPE: DNA
<213> ORGANISM: Homo sapiens

<400> SEQUENCE: 34
tgcagtgcta gagatcccaa caggggtgg aacaccgggg agctgttttt t 51

<210> SEQ ID NO 35
<211> LENGTH: 36
<212> TYPE: DNA
<213> ORGANISM: Homo sapiens

<400> SEQUENCE: 35
tgtgctacgg actctggcac cgacaagctc atcttt 36

<210> SEQ ID NO 36
<211> LENGTH: 48
<212> TYPE: DNA
<213> ORGANISM: Homo sapiens

<400> SEQUENCE: 36
tgtgccagca gcttggatcg ggtggggaca gggaccgagc agtacttc 48

<210> SEQ ID NO 37
<211> LENGTH: 45
<212> TYPE: DNA
<213> ORGANISM: Homo sapiens

```
<400> SEQUENCE: 37
tgtgcagaga gtaaacggaa aacctcctac gacaaggtga tattt            45

<210> SEQ ID NO 38
<211> LENGTH: 42
<212> TYPE: DNA
<213> ORGANISM: Homo sapiens

<400> SEQUENCE: 38
tgtgccagca gcccctcaac ggggcaagag acccagtact tc               42

<210> SEQ ID NO 39
<211> LENGTH: 48
<212> TYPE: DNA
<213> ORGANISM: Homo sapiens

<400> SEQUENCE: 39
tgtgctgtgc aggccgttag tggaggtagc aactataaac tgacattt          48

<210> SEQ ID NO 40
<211> LENGTH: 39
<212> TYPE: DNA
<213> ORGANISM: Homo sapiens

<400> SEQUENCE: 40
tgtgcctgga gtccccaaac aacagggtta gagtacttc                   39

<210> SEQ ID NO 41
<211> LENGTH: 45
<212> TYPE: DNA
<213> ORGANISM: Homo sapiens

<400> SEQUENCE: 41
tgtgctgtga gtgatgggga taactatggt cagaattttg tcttt             45

<210> SEQ ID NO 42
<211> LENGTH: 33
<212> TYPE: DNA
<213> ORGANISM: Homo sapiens

<400> SEQUENCE: 42
tgtgccagca gcttacagat agctcagtac ttc                         33

<210> SEQ ID NO 43
<211> LENGTH: 42
<212> TYPE: DNA
<213> ORGANISM: Homo sapiens

<400> SEQUENCE: 43
tgtgctggcc tggagggccc aaacgactac aagctcagct tt                42

<210> SEQ ID NO 44
<211> LENGTH: 42
<212> TYPE: DNA
<213> ORGANISM: Homo sapiens

<400> SEQUENCE: 44
tgtgccaccg cctcacaggg gccaaaagag acccagtact tc                42

<210> SEQ ID NO 45
<211> LENGTH: 33
<212> TYPE: DNA
<213> ORGANISM: Homo sapiens
```

```
<400> SEQUENCE: 45
tgtgcagcaa acagagatga caagatcatc ttt                           33

<210> SEQ ID NO 46
<211> LENGTH: 39
<212> TYPE: DNA
<213> ORGANISM: Homo sapiens

<400> SEQUENCE: 46
tgtgccagcg gaatacaggg tacctacgag cagtacttc                     39

<210> SEQ ID NO 47
<211> LENGTH: 36
<212> TYPE: DNA
<213> ORGANISM: Homo sapiens

<400> SEQUENCE: 47
tgtgctctaa ggcagggagc ccagaagctg gtattt                        36

<210> SEQ ID NO 48
<211> LENGTH: 51
<212> TYPE: DNA
<213> ORGANISM: Homo sapiens

<400> SEQUENCE: 48
tgcagcgttg ataggtcttc tagcgggtcg aacaccgggg agctgttttt t        51

<210> SEQ ID NO 49
<211> LENGTH: 30
<212> TYPE: DNA
<213> ORGANISM: Homo sapiens

<400> SEQUENCE: 49
tgtgccgcta acaatgccag actcatgttt                               30

<210> SEQ ID NO 50
<211> LENGTH: 42
<212> TYPE: DNA
<213> ORGANISM: Homo sapiens

<400> SEQUENCE: 50
tgtgccagca gcctcggggg gtcggtagag acccagtact tc                 42

<210> SEQ ID NO 51
<211> LENGTH: 39
<212> TYPE: DNA
<213> ORGANISM: Homo sapiens

<400> SEQUENCE: 51
tgtgctgtgg gtacaacagg aacctacaaa tacatctttt                    39

<210> SEQ ID NO 52
<211> LENGTH: 39
<212> TYPE: DNA
<213> ORGANISM: Homo sapiens

<400> SEQUENCE: 52
tgtgccagca gttctagggg ggcacagccc cagcattttt                    39

<210> SEQ ID NO 53
<211> LENGTH: 36
<212> TYPE: DNA
```

<213> ORGANISM: Homo sapiens

<400> SEQUENCE: 53
tgtgctctaa gtacaggctt tcagaaactt gtattt                     36

<210> SEQ ID NO 54
<211> LENGTH: 48
<212> TYPE: DNA
<213> ORGANISM: Homo sapiens

<400> SEQUENCE: 54
tgtgccagca gcccactagg cgcgagctcc tacaatgagc agttcttc         48

<210> SEQ ID NO 55
<211> LENGTH: 39
<212> TYPE: DNA
<213> ORGANISM: Homo sapiens

<400> SEQUENCE: 55
tgtgctgtga gagccgctgg caccgacaag ctcatcttt                  39

<210> SEQ ID NO 56
<211> LENGTH: 45
<212> TYPE: DNA
<213> ORGANISM: Homo sapiens

<400> SEQUENCE: 56
tgtgcaatga gcgcgaggtc tgggggttac cagaaagtta cctttt          45

<210> SEQ ID NO 57
<211> LENGTH: 42
<212> TYPE: DNA
<213> ORGANISM: Homo sapiens

<400> SEQUENCE: 57
tgtgccagca gcccgggcag ggaaagcggg gagctgtttt tt              42

<210> SEQ ID NO 58
<211> LENGTH: 39
<212> TYPE: DNA
<213> ORGANISM: Homo sapiens

<400> SEQUENCE: 58
tgtgctctaa gggcttataa caccgacaag ctcatcttt                  39

<210> SEQ ID NO 59
<211> LENGTH: 45
<212> TYPE: DNA
<213> ORGANISM: Homo sapiens

<400> SEQUENCE: 59
tgtgccagca gcttagcgac cgggacagca tacgagcagt acttc           45

<210> SEQ ID NO 60
<211> LENGTH: 14
<212> TYPE: PRT
<213> ORGANISM: Homo sapiens

<400> SEQUENCE: 60

Cys Ala Val Gly Ser Ser Ser Asn Thr Gly Lys Leu Ile Phe
1               5                   10

<210> SEQ ID NO 61

```
<211> LENGTH: 17
<212> TYPE: PRT
<213> ORGANISM: Homo sapiens

<400> SEQUENCE: 61

Cys Ala Ser Ser Gln Asp Ala Ile Gly Thr Gly Val Leu Lys Leu Phe
1               5                   10                  15

Phe

<210> SEQ ID NO 62
<211> LENGTH: 12
<212> TYPE: PRT
<213> ORGANISM: Homo sapiens

<400> SEQUENCE: 62

Cys Ala Ala Ser Phe Gly Asn Glu Lys Leu Thr Phe
1               5                   10

<210> SEQ ID NO 63
<211> LENGTH: 15
<212> TYPE: PRT
<213> ORGANISM: Homo sapiens

<400> SEQUENCE: 63

Cys Ala Ser Ser Ala Ser Asp Arg Glu Thr Tyr Gly Tyr Thr Phe
1               5                   10                  15

<210> SEQ ID NO 64
<211> LENGTH: 14
<212> TYPE: PRT
<213> ORGANISM: Homo sapiens

<400> SEQUENCE: 64

Cys Ala Glu Ala Gly Gly Thr Ser Tyr Gly Lys Leu Thr Phe
1               5                   10

<210> SEQ ID NO 65
<211> LENGTH: 14
<212> TYPE: PRT
<213> ORGANISM: Homo sapiens

<400> SEQUENCE: 65

Cys Ala Ser Cys Arg Thr Ser Ser Tyr Asn Glu Gln Phe Phe
1               5                   10

<210> SEQ ID NO 66
<211> LENGTH: 13
<212> TYPE: PRT
<213> ORGANISM: Homo sapiens

<400> SEQUENCE: 66

Cys Ala Ser Ser Phe Thr Ser Thr Asp Thr Gln Tyr Phe
1               5                   10

<210> SEQ ID NO 67
<211> LENGTH: 13
<212> TYPE: PRT
<213> ORGANISM: Homo sapiens

<400> SEQUENCE: 67

Cys Ala Ala Pro Ser Gly Asn Thr Gly Lys Leu Ile Phe
1               5                   10

<210> SEQ ID NO 68
```

```
<211> LENGTH: 14
<212> TYPE: PRT
<213> ORGANISM: Homo sapiens

<400> SEQUENCE: 68

Cys Ala Ser Thr Ile Ala Gly Gly Glu Asp Thr Gln Tyr Phe
1               5                   10

<210> SEQ ID NO 69
<211> LENGTH: 10
<212> TYPE: PRT
<213> ORGANISM: Homo sapiens

<400> SEQUENCE: 69

Cys Ala Val Thr Gly Asn Gln Phe Tyr Phe
1               5                   10

<210> SEQ ID NO 70
<211> LENGTH: 14
<212> TYPE: PRT
<213> ORGANISM: Homo sapiens

<400> SEQUENCE: 70

Cys Ala Ala Ser Val Gly Ser Asp Gly Gln Lys Leu Leu Phe
1               5                   10

<210> SEQ ID NO 71
<211> LENGTH: 15
<212> TYPE: PRT
<213> ORGANISM: Homo sapiens

<400> SEQUENCE: 71

Cys Ala Ser Ser Phe Phe Arg Arg Asp Gly Glu Thr Gln Tyr Phe
1               5                   10                  15

<210> SEQ ID NO 72
<211> LENGTH: 18
<212> TYPE: PRT
<213> ORGANISM: Homo sapiens

<400> SEQUENCE: 72

Cys Val Val Ser Asp Asn Arg Ala Gly Gly Thr Ser Tyr Gly Lys Leu
1               5                   10                  15

Thr Phe

<210> SEQ ID NO 73
<211> LENGTH: 14
<212> TYPE: PRT
<213> ORGANISM: Homo sapiens

<400> SEQUENCE: 73

Cys Ala Glu Asn Ser Gly Gly Ser Asn Tyr Lys Leu Thr Phe
1               5                   10

<210> SEQ ID NO 74
<211> LENGTH: 14
<212> TYPE: PRT
<213> ORGANISM: Homo sapiens

<400> SEQUENCE: 74

Cys Ala Ser Thr Ala Gly Ala Ser Asp Gln Pro Gln His Phe
1               5                   10

<210> SEQ ID NO 75
```

```
<211> LENGTH: 13
<212> TYPE: PRT
<213> ORGANISM: Homo sapiens

<400> SEQUENCE: 75

Cys Ala Ser Arg Asn Asn Ala Gly Asn Met Leu Thr Phe
1               5                   10

<210> SEQ ID NO 76
<211> LENGTH: 16
<212> TYPE: PRT
<213> ORGANISM: Homo sapiens

<400> SEQUENCE: 76

Cys Ala Ser Ser Tyr Ser Asn Arg Gly Tyr Asn Ser Pro Leu His Phe
1               5                   10                  15

<210> SEQ ID NO 77
<211> LENGTH: 12
<212> TYPE: PRT
<213> ORGANISM: Homo sapiens

<400> SEQUENCE: 77

Cys Ala Thr Asp Glu Gly Asn Glu Lys Leu Thr Phe
1               5                   10

<210> SEQ ID NO 78
<211> LENGTH: 14
<212> TYPE: PRT
<213> ORGANISM: Homo sapiens

<400> SEQUENCE: 78

Cys Ala Ser Ser Leu Val Gly Val Ser Tyr Glu Gln Tyr Phe
1               5                   10

<210> SEQ ID NO 79
<211> LENGTH: 13
<212> TYPE: PRT
<213> ORGANISM: Homo sapiens

<400> SEQUENCE: 79

Cys Ala Glu Ala Val Tyr Gly Asn Asn Arg Leu Ala Phe
1               5                   10

<210> SEQ ID NO 80
<211> LENGTH: 14
<212> TYPE: PRT
<213> ORGANISM: Homo sapiens

<400> SEQUENCE: 80

Cys Ala Ser Asp Arg Thr Gly Ser Asp Thr Glu Ala Phe Phe
1               5                   10

<210> SEQ ID NO 81
<211> LENGTH: 12
<212> TYPE: PRT
<213> ORGANISM: Homo sapiens

<400> SEQUENCE: 81

Cys Ala Val Asp Asn Tyr Gly Gln Asn Phe Val Phe
1               5                   10

<210> SEQ ID NO 82
<211> LENGTH: 15
<212> TYPE: PRT
```

<213> ORGANISM: Homo sapiens

<400> SEQUENCE: 82

Cys Ile Val Lys Gly Gly Gly Tyr Asn Phe Asn Lys Phe Tyr Phe
1               5                   10                  15

<210> SEQ ID NO 83
<211> LENGTH: 14
<212> TYPE: PRT
<213> ORGANISM: Homo sapiens

<400> SEQUENCE: 83

Cys Ala Ser Ser Met Gly Val Gly Asp Thr Glu Ala Phe Phe
1               5                   10

<210> SEQ ID NO 84
<211> LENGTH: 13
<212> TYPE: PRT
<213> ORGANISM: Homo sapiens

<400> SEQUENCE: 84

Cys Ala Thr Asp Gly Gly Gly Ala Gln Lys Leu Val Phe
1               5                   10

<210> SEQ ID NO 85
<211> LENGTH: 14
<212> TYPE: PRT
<213> ORGANISM: Homo sapiens

<400> SEQUENCE: 85

Cys Ala Ser Thr Gly Gln Gly Ile Gly Asn Thr Ile Tyr Phe
1               5                   10

<210> SEQ ID NO 86
<211> LENGTH: 14
<212> TYPE: PRT
<213> ORGANISM: Homo sapiens

<400> SEQUENCE: 86

Cys Ala Leu Tyr Ser Gly Gly Ser Asn Tyr Lys Leu Thr Phe
1               5                   10

<210> SEQ ID NO 87
<211> LENGTH: 12
<212> TYPE: PRT
<213> ORGANISM: Homo sapiens

<400> SEQUENCE: 87

Cys Ala Met Ser Leu Asn Asp Tyr Lys Leu Ser Phe
1               5                   10

<210> SEQ ID NO 88
<211> LENGTH: 12
<212> TYPE: PRT
<213> ORGANISM: Homo sapiens

<400> SEQUENCE: 88

Cys Ser Ala Asn Asp Gly Thr Asp Thr Gln Tyr Phe
1               5                   10

<210> SEQ ID NO 89
<211> LENGTH: 12
<212> TYPE: PRT
<213> ORGANISM: Homo sapiens

```
<400> SEQUENCE: 89

Cys Ala Ala Pro Gly Gly Asp Asp Lys Ile Ile Phe
1               5                   10

<210> SEQ ID NO 90
<211> LENGTH: 14
<212> TYPE: PRT
<213> ORGANISM: Homo sapiens

<400> SEQUENCE: 90

Cys Ala Leu Ala Gln Thr Asp Ser Trp Gly Lys Phe Gln Phe
1               5                   10

<210> SEQ ID NO 91
<211> LENGTH: 14
<212> TYPE: PRT
<213> ORGANISM: Homo sapiens

<400> SEQUENCE: 91

Cys Ala Ser Ser Leu Pro Gly Gln Ala Tyr Glu Gln Tyr Phe
1               5                   10

<210> SEQ ID NO 92
<211> LENGTH: 17
<212> TYPE: PRT
<213> ORGANISM: Homo sapiens

<400> SEQUENCE: 92

Cys Ala Val Ser Asp Gln Lys Leu Thr Gly Gly Gly Asn Lys Leu Thr
1               5                   10                  15

Phe

<210> SEQ ID NO 93
<211> LENGTH: 17
<212> TYPE: PRT
<213> ORGANISM: Homo sapiens

<400> SEQUENCE: 93

Cys Ser Ala Arg Asp Pro Asn Arg Gly Trp Asn Thr Gly Glu Leu Phe
1               5                   10                  15

Phe

<210> SEQ ID NO 94
<211> LENGTH: 12
<212> TYPE: PRT
<213> ORGANISM: Homo sapiens

<400> SEQUENCE: 94

Cys Ala Thr Asp Ser Gly Thr Asp Lys Leu Ile Phe
1               5                   10

<210> SEQ ID NO 95
<211> LENGTH: 16
<212> TYPE: PRT
<213> ORGANISM: Homo sapiens

<400> SEQUENCE: 95

Cys Ala Ser Ser Leu Asp Arg Val Gly Thr Gly Thr Glu Gln Tyr Phe
1               5                   10                  15

<210> SEQ ID NO 96
<211> LENGTH: 15
<212> TYPE: PRT
```

```
<213> ORGANISM: Homo sapiens

<400> SEQUENCE: 96

Cys Ala Glu Ser Lys Arg Lys Thr Ser Tyr Asp Lys Val Ile Phe
1               5                   10                  15

<210> SEQ ID NO 97
<211> LENGTH: 14
<212> TYPE: PRT
<213> ORGANISM: Homo sapiens

<400> SEQUENCE: 97

Cys Ala Ser Ser Pro Ser Thr Gly Gln Glu Thr Gln Tyr Phe
1               5                   10

<210> SEQ ID NO 98
<211> LENGTH: 16
<212> TYPE: PRT
<213> ORGANISM: Homo sapiens

<400> SEQUENCE: 98

Cys Ala Val Gln Ala Val Ser Gly Gly Ser Asn Tyr Lys Leu Thr Phe
1               5                   10                  15

<210> SEQ ID NO 99
<211> LENGTH: 13
<212> TYPE: PRT
<213> ORGANISM: Homo sapiens

<400> SEQUENCE: 99

Cys Ala Trp Ser Pro Gln Thr Thr Gly Leu Glu Tyr Phe
1               5                   10

<210> SEQ ID NO 100
<211> LENGTH: 15
<212> TYPE: PRT
<213> ORGANISM: Homo sapiens

<400> SEQUENCE: 100

Cys Ala Val Ser Asp Gly Asp Asn Tyr Gly Gln Asn Phe Val Phe
1               5                   10                  15

<210> SEQ ID NO 101
<211> LENGTH: 11
<212> TYPE: PRT
<213> ORGANISM: Homo sapiens

<400> SEQUENCE: 101

Cys Ala Ser Ser Leu Gln Ile Ala Gln Tyr Phe
1               5                   10

<210> SEQ ID NO 102
<211> LENGTH: 14
<212> TYPE: PRT
<213> ORGANISM: Homo sapiens

<400> SEQUENCE: 102

Cys Ala Gly Leu Glu Gly Pro Asn Asp Tyr Lys Leu Ser Phe
1               5                   10

<210> SEQ ID NO 103
<211> LENGTH: 14
<212> TYPE: PRT
<213> ORGANISM: Homo sapiens
```

```
<400> SEQUENCE: 103

Cys Ala Thr Ala Ser Gln Gly Pro Lys Glu Thr Gln Tyr Phe
1               5                   10

<210> SEQ ID NO 104
<211> LENGTH: 11
<212> TYPE: PRT
<213> ORGANISM: Homo sapiens

<400> SEQUENCE: 104

Cys Ala Ala Asn Arg Asp Asp Lys Ile Ile Phe
1               5                   10

<210> SEQ ID NO 105
<211> LENGTH: 13
<212> TYPE: PRT
<213> ORGANISM: Homo sapiens

<400> SEQUENCE: 105

Cys Ala Ser Gly Ile Gln Gly Thr Tyr Glu Gln Tyr Phe
1               5                   10

<210> SEQ ID NO 106
<211> LENGTH: 12
<212> TYPE: PRT
<213> ORGANISM: Homo sapiens

<400> SEQUENCE: 106

Cys Ala Leu Arg Gln Gly Ala Gln Lys Leu Val Phe
1               5                   10

<210> SEQ ID NO 107
<211> LENGTH: 17
<212> TYPE: PRT
<213> ORGANISM: Homo sapiens

<400> SEQUENCE: 107

Cys Ser Val Asp Arg Ser Ser Gly Ser Asn Thr Gly Glu Leu Phe
1               5                   10                  15

Phe

<210> SEQ ID NO 108
<211> LENGTH: 10
<212> TYPE: PRT
<213> ORGANISM: Homo sapiens

<400> SEQUENCE: 108

Cys Ala Ala Asn Asn Ala Arg Leu Met Phe
1               5                   10

<210> SEQ ID NO 109
<211> LENGTH: 14
<212> TYPE: PRT
<213> ORGANISM: Homo sapiens

<400> SEQUENCE: 109

Cys Ala Ser Ser Leu Gly Gly Ser Val Glu Thr Gln Tyr Phe
1               5                   10

<210> SEQ ID NO 110
<211> LENGTH: 13
<212> TYPE: PRT
<213> ORGANISM: Homo sapiens
```

```
<400> SEQUENCE: 110

Cys Ala Val Gly Thr Thr Gly Thr Tyr Lys Tyr Ile Phe
1               5                   10

<210> SEQ ID NO 111
<211> LENGTH: 13
<212> TYPE: PRT
<213> ORGANISM: Homo sapiens

<400> SEQUENCE: 111

Cys Ala Ser Ser Ser Arg Gly Ala Gln Pro Gln His Phe
1               5                   10

<210> SEQ ID NO 112
<211> LENGTH: 12
<212> TYPE: PRT
<213> ORGANISM: Homo sapiens

<400> SEQUENCE: 112

Cys Ala Leu Ser Thr Gly Phe Gln Lys Leu Val Phe
1               5                   10

<210> SEQ ID NO 113
<211> LENGTH: 16
<212> TYPE: PRT
<213> ORGANISM: Homo sapiens

<400> SEQUENCE: 113

Cys Ala Ser Ser Pro Leu Gly Ala Ser Ser Tyr Asn Glu Gln Phe Phe
1               5                   10                  15

<210> SEQ ID NO 114
<211> LENGTH: 13
<212> TYPE: PRT
<213> ORGANISM: Homo sapiens

<400> SEQUENCE: 114

Cys Ala Val Arg Ala Ala Gly Thr Asp Lys Leu Ile Phe
1               5                   10

<210> SEQ ID NO 115
<211> LENGTH: 15
<212> TYPE: PRT
<213> ORGANISM: Homo sapiens

<400> SEQUENCE: 115

Cys Ala Met Ser Ala Arg Ser Gly Gly Tyr Gln Lys Val Thr Phe
1               5                   10                  15

<210> SEQ ID NO 116
<211> LENGTH: 14
<212> TYPE: PRT
<213> ORGANISM: Homo sapiens

<400> SEQUENCE: 116

Cys Ala Ser Ser Pro Gly Arg Glu Ser Gly Glu Leu Phe Phe
1               5                   10

<210> SEQ ID NO 117
<211> LENGTH: 13
<212> TYPE: PRT
<213> ORGANISM: Homo sapiens

<400> SEQUENCE: 117
```

Cys Ala Leu Arg Ala Tyr Asn Thr Asp Lys Leu Ile Phe
1               5                   10

<210> SEQ ID NO 118
<211> LENGTH: 15
<212> TYPE: PRT
<213> ORGANISM: Homo sapiens

<400> SEQUENCE: 118

Cys Ala Ser Ser Leu Ala Thr Gly Thr Ala Tyr Glu Gln Tyr Phe
1               5                   10                  15

<210> SEQ ID NO 119
<211> LENGTH: 28
<212> TYPE: DNA
<213> ORGANISM: Artificial Sequence
<220> FEATURE:
<223> OTHER INFORMATION: Description of Artificial Sequence: Synthetic
      reverse primer for the amplification of TCR
      alpha-chain

<400> SEQUENCE: 119
cacaggctgt cttacaatct tgcagatc                                              28

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic
      reverse primer for the amplification of TCR
      beta-chain

<400> SEQUENCE: 120
ctccacttcc agggctgcct tca                                                   23

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      reverse primer for the amplification of TCR
      beta-chain

<400> SEQUENCE: 121
tgacctggga tggttttgga gcta                                                  24

<210> SEQ ID NO 122
<211> LENGTH: 17
<212> TYPE: DNA
<213> ORGANISM: Artificial Sequence
<220> FEATURE:
<223> OTHER INFORMATION: Description of Artificial Sequence: Synthetic
      primer for determination of a CDR3 nucleotide
      sequence

<400> SEQUENCE: 122
caggaaacag ctatgac                                                          17

<210> SEQ ID NO 123
<211> LENGTH: 16
<212> TYPE: PRT
<213> ORGANISM: Homo sapiens

<400> SEQUENCE: 123

Lys Arg Tyr Phe Lys Leu Ser His Leu Gln Met His Ser Arg Lys His

```
<210> SEQ ID NO 124
<211> LENGTH: 20
<212> TYPE: PRT
<213> ORGANISM: Homo sapiens

<400> SEQUENCE: 124

Phe Arg Lys Gln Asn Pro Asp Ile Val Ile Tyr Gln Tyr Met Asp Asp
1               5                   10                  15

Leu Tyr Val Gly
            20

<210> SEQ ID NO 125
<211> LENGTH: 9
<212> TYPE: PRT
<213> ORGANISM: Homo sapiens

<400> SEQUENCE: 125

Cys Tyr Thr Trp Asn Gln Met Asn Leu
1               5
```

ANTIGEN-SPECIFIC HELPER T-CELL RECEPTOR GENES

TECHNICAL FIELD

The present invention relates to polynucleotides contained in T cell receptor (TCR) genes of cancer antigen-specific helper T-cells. In particular, the present invention relates to polynucleotides encoding complementarity determining region 3 (CDR3) of each α-chain and α-chain of TCR of CD4$^+$ helper T-cells specific to a WT1 helper peptide having an amino acid sequence shown in SEQ ID NO: 123. The present invention also relates to polypeptides encoded by these polynucleotides. Further, the present invention relates to CD4$^+$ T-cells into which TCR genes containing these polynucleotides are introduced, induction and enhancement of WT1-specific cytotoxic T cells (WT1-specific CTL) using them, and treatment of cancers using them, and so on.

SEQUENCE LISTING

The instant application contains a Sequence Listing which has been submitted electronically in ASCII format and is hereby incorporated by reference in its entirety. Said ASCII copy, created on Sep. 24, 2015, is named 05273.0155_SL.txt and is 21,271 bytes in size.

BACKGROUND ART

WT1 gene (Wilms' tumor 1 gene) is a gene which was identified as a gene responsible for Wilms tumor which is a renal cancer in children (Non-patent Documents 1 and 2). WT1 is a transcription factor having a zinc finger structure. Initially, WT1 gene was considered to be a tumor suppressor gene. However, subsequent studies (Non-patent Documents 3, 4, 5 and 6) showed that WT1 gene rather functions as an oncogene in hematopoietic tumors and solid cancers.

It was showed that peptide-specific cytotoxic T cells (CTLs) were induced by stimulating peripheral mononuclear cells in vitro using a WT1 peptide and that these CTLs damage tumor and cancer cells in hematopoietic tumors and solid cancers which express WT1 endogenously. Because CTL recognizes a WT1 peptide in a form of a complex in which the WT1 peptide is bound to a MHC class I molecule, such a WT1 peptide differs in accordance to MHC class I subtype (Patent Document 1, Non-Patent Document 7, Patent Documents 2, 3 and 4).

Existence of helper T cells specific to a cancer antigen is important for effective induction of CTL (Non-Patent Document 8). Helper T cells are induced and activated by recognizing a complex of a MHC class II molecule and an antigen peptide on antigen-presenting cells. Activated helper T cells produce cytokines such as IL-2, IL-4, IL-5, IL-6, or interferons, and help proliferation, differentiation and maturation of B cells. Activated helper T cells also have a function to promote proliferation, differentiation and maturation of other subset of T cells (such as Tc cells). Thus, because activated helper T cells have a function to activate immune system by promoting proliferation and activation of B cells and T cells, it is considered that enhancing the function of helper T cells via a MHC class II binding antigen peptide (helper peptide) to enhance the effect of a cancer vaccine is useful in cancer immunotherapy (Non-Patent Document 9).

Examples of helper peptides relating to WT1 which are presently recognized are a peptide binding to HLA-DRB1*04:01 molecule (Non-Patent Document 10), a peptide binding to HLA-DRB1*04:05 molecule, a peptide binding to HLA-DRB1*15:02 molecule (Patent Document 5), a peptide binding to HLA-DRB1*04:05 molecule, HLA-DRB1*15:02 molecule, HLA-DRB*15:01 molecule, HLA-DPB1*09:01 molecule and HLA-DPB1*05:01 molecule (Patent Document 6).

However, sequences of T cell receptor (TCR) genes of antigen-specific CD4$^+$ helper T-cells which recognize a helper peptide have not been known at all.

DOCUMENTS OF BACKGROUND ART

Patent Documents

Patent Document 1: WO2003/106682
Patent Document 2: WO2005/095598
Patent Document 3: WO2007/097358
Patent Document 4: PCT/JP2007/074146
Patent Document 5: WO2005/045027
Patent Document 6: WO2008/105462

Non-Patent Documents

Non-Patent Document 1: Daniel A. Haber et al., Cell. 1990 Jun. 29; 61(7):1257-69.
Non-Patent Document 2: Call K M et al., Cell. 1990 Feb. 9; 60(3):509-20.
Non-Patent Document 3: Menke A L et al., Int Rev Cytol. 1998; 181:151-212. Review.
Non-Patent Document 4: Yamagami T et al., Blood. 1996 Apr. 1; 87(7):2878-84.
Non-Patent Document 5: Inoue K et al., Blood. 1998 Apr. 15; 91(8):2969-76.
Non-Patent Document 6: Tsuboi A et al., Leuk Res. 1999 May; 23(5):499-505.
Non-Patent Document 7: Oka Y et al., Immunogenetics. 2000 February; 51(2):99-107.
Non-Patent Document 8: Gao F G et al., Cancer Res. 2002 Nov. 15; 62(22):6438-41.
Non-Patent Document 9: Zeng G, J Immunother. 2001 May; 24(3):195-204.
Non-Patent Document 10: Knights A J et al., Cancer Immunol Immunother. 2002 July; 51(5):271-81.

SUMMARY OF INVENTION

Problem to be Solved by the Invention

Problems to be solved by the invention were to determine sequences of TCR genes of CD4$^+$ helper T-cells specific to a WT1 helper peptide, to obtain CD4$^+$ T-cells into which these TCR genes have been introduced, to enhance induction of WT1 specific CTL using such cells, and to treat or prevent cancers, and so on.

Means to Solve the Problem

The inventors studied vary hard to solve the above problems, and succeeded in isolating α-chain genes and β-chain genes of TCR of CD4$^+$ helper T-cells specific to a WT1 helper peptide, and determined each CDR3 sequence. Further, the inventors introduced TCR genes containing the sequences thus determined into CD4$^+$ T-cells, and succeeded in enhancing induction of WT1 specific CTL and damaging WT1 expressing cancer cells by use of the CD4$^+$ T-cells. Thus, the inventors have completed the present invention.

That is, the present invention provides:

(1) A polynucleotide (referred as "αCDR3 polynucleotide") having a nucleotide sequence selected from the group consisting of SEQ ID NOs: 1, 3, 5, 8, 10, 11, 13, 14, 16, 18, 20, 22, 23, 25, 27, 28, 30, 31, 33, 35, 37, 39, 41, 43, 45, 47, 49, 51, 53, 55, 56 and 58, wherein said polynucleotide encodes CDR3 of α-chain of TCR of a CD4⁺ helper T-cell specific to a WT1 helper peptide (WT1$_{332}$ peptide) having an amino acid sequence shown in SEQ ID NO: 123 or a variant sequence thereof.

(2) A polynucleotide (referred as "βCDR3 polynucleotide") having a nucleotide sequence selected from the group consisting of SEQ ID NOs: 2, 4, 6, 7, 9, 12, 15, 17, 19, 21, 24, 26, 29, 32, 34, 36, 38, 40, 42, 44, 46, 48, 50, 52, 54, 57 and 59, wherein said polynucleotide encodes CDR3 of β-chain of TCR of a CD4⁺ helper T-cell specific to WT1$_{332}$ peptide.

(3) A pair of a αCDR3 polynucleotide and a βCDR3 polynucleotide, wherein each polynucleotide has the following nucleotide sequence:

| α CDR3 polynucleotide | βCDR3 polynucleotide |
|---|---|
| SEQ ID NO: 1 | SEQ ID NO: 2 |
| SEQ ID NO: 3 | SEQ ID NO: 4 |
| SEQ ID NO: 5 | SEQ ID NO: 6 |
| SEQ ID NO: 3 | SEQ ID NO: 7 |
| SEQ ID NO: 8 | SEQ ID NO: 9 |
| SEQ ID NO: 10 | SEQ ID NO: 12 |
| SEQ ID NO: 11 | SEQ ID NO: 12 |
| SEQ ID NO: 13 | SEQ ID NO: 15 |
| SEQ ID NO: 14 | SEQ ID NO: 15 |
| SEQ ID NO: 16 | SEQ ID NO: 17 |
| SEQ ID NO: 18 | SEQ ID NO: 19 |
| SEQ ID NO: 20 | SEQ ID NO: 21 |
| SEQ ID NO: 22 | SEQ ID NO: 24 |
| SEQ ID NO: 23 | SEQ ID NO: 24 |
| SEQ ID NO: 25 | SEQ ID NO: 26 |
| SEQ ID NO: 27 | SEQ ID NO: 4 |
| SEQ ID NO: 28 | SEQ ID NO: 29 |
| SEQ ID NO: 30 | SEQ ID NO: 32 |
| SEQ ID NO: 31 | SEQ ID NO: 32 |
| SEQ ID NO: 33 | SEQ ID NO: 34 |
| SEQ ID NO: 35 | SEQ ID NO: 36 |
| SEQ ID NO: 37 | SEQ ID NO: 38 |
| SEQ ID NO: 39 | SEQ ID NO: 40 |
| SEQ ID NO: 41 | SEQ ID NO: 42 |
| SEQ ID NO: 43 | SEQ ID NO: 44 |
| SEQ ID NO: 45 | SEQ ID NO: 46 |
| SEQ ID NO: 47 | SEQ ID NO: 48 |
| SEQ ID NO: 49 | SEQ ID NO: 50 |
| SEQ ID NO: 51 | SEQ ID NO: 52 |
| SEQ ID NO: 53 | SEQ ID NO: 54 |
| SEQ ID NO: 55 | SEQ ID NO: 57 |
| SEQ ID NO: 56 | SEQ ID NO: 57 |
| SEQ ID NO: 58 | SEQ ID NO: 59 | provided that said sequence may be a complementary sequence or a degenerate sequence thereof.

(4) A TCR gene comprising the αCDR3 polynucleotide and the βCDR3 polynucleotide in any one of pairs of (3).

(5) The TCR gene of (4) obtainable from a CD4⁺ T-cell specific to WT1$_{332}$ peptide.

(6) A method for producing a CD4⁺ helper cell specific to WT1$_{332}$ peptide, comprising introducing the TCR gene of (4) into a CD4⁺ T cell.

(7) A CD4⁺ helper T-cell obtainable by the method of (5).

(8) A vector comprising a TCR gene which comprises the αCDR3 polynucleotide and the βCDR3 polynucleotide in any one of pairs of (3).

(9) The method of (6) wherein said introduction is performed using the vector of (8).

(10) A method for enhancing the induction of a WT1 specific CTL, comprising co-culturing the CD4⁺ helper T-cell of (7) and a peripheral mononuclear cell.

(11) A WT1-specific CTL obtainable by the method of (10).

(12) A method for the treatment or prevention of a cancer in a subject, comprising introducing the CD4⁺ helper T-cell of (7) into the subject.

(13) A pharmaceutical composition for the treatment or prevention of a cancer, comprising the CD4⁺ helper T-cell of (7).

(14) Use of the CD4⁺ helper T-cell of (7) for the manufacture of a medicine for the treatment or prevention of a cancer.

(15) A DNA chip comprising the αCDR3 polynucleotide of (1), the βCDR3 polynucleotide of (2), or both of the αCDR3 polynucleotide of (1) and the βCDR3 polynucleotide of (2).

(16) A method for measuring the frequency of CD4⁺ helper T-cell specific to WT1$_{332}$ peptide in a sample, comprising using the DNA chip of (15).

(17) An αCDR3 peptide encoded by any one of the αCDR3 polynucleotides of (1).

(18) A βCDR3 peptide encoded by any one of the βCDR3 polynucleotides of (2).

(19) A pair of peptides encoded by any one of pairs of the polynucleotides of (3).

(20) A chip comprising the peptide of (17) or (18), or the pair of the peptides of (19).

(21) An antibody against any one of the peptides of any one of (17)-(19).

(22) A method for measuring the frequency of CD4⁺ helper T-cell specific to WT1$_{332}$ peptide in a sample, comprising using the antibody of (21).

Effect of the Invention

According to the present invention, a CD4⁺ helper T-cell is obtained into which a TCR gene having the CDR3 nucleotide sequence determined by the present invention has been introduced. A WT1-specific CTL can be induced using said CD4⁺ helper T-cell, and a cancer can be treated or prevented effectively. Further, a DNA chip is prepared using the TCR sequences, and frequency of WT1$_{332}$-specific CD4⁺ helper T-cells in a sample can be measured.

BRIEF DESCRIPTION OF DRAWINGS

FIG. 1A shows nucleotide sequences of CDR3 α-chains and α-chains of TCR of CD4⁺ helper T-cells obtained by the present invention, and amino acid sequences of CDR3 encoded thereby. Number in parentheses positioned at the right end of each sequence presents SEQ ID NOs in SEQUENCE LISTING. V-GENE, J-GENE and J-GENE describe V region, J region and D region in individual genes, respectively.

FIG. 1B shows nucleotide sequences of CDR3 α-chains and β-chains of TCR of CD4⁺ helper T-cells obtained by the present invention, and amino acid sequences of CDR3 encoded thereby. Number in parentheses positioned at the right end of each sequence presents SEQ ID NOs in SEQUENCE LISTING. V-GENE, J-GENE and J-GENE describe V region, J region and D region in individual genes, respectively.

DESCRIPTION OF EMBODIMENTS

Figure 2A:
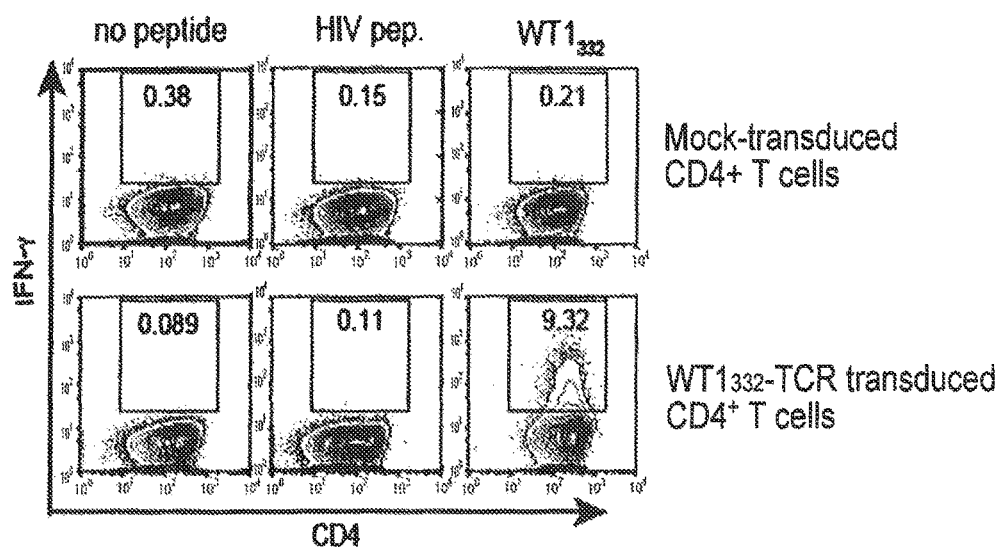
FIG. 2A shows interferon-γ production by WT1$_{332}$-specific CD4⁺ helper T-cells into which TCR genes shown in Table 3 have been introduced.
Figure 2B:
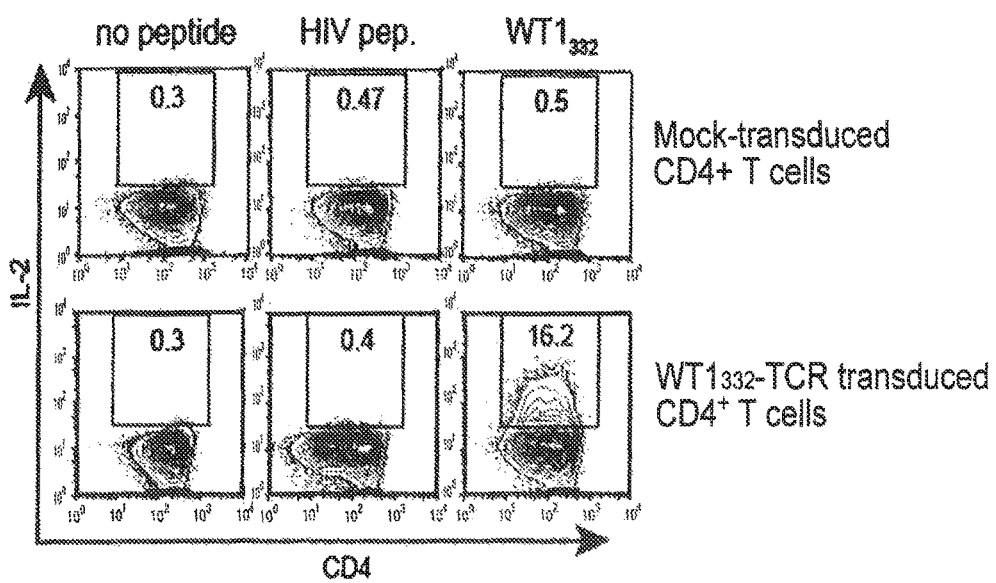
FIG. 2B shows IL-2 production by WT1$_{332}$-specific CD4⁺ helper T-cells into which TCR genes shown in Table 3 have been introduced.

The present invention is based on the determination of the polynucleotides encoding α-chain containing CDR3 (hereinafter referred as "αCDR3 polynucleotide") and the polynucleotides encoding β-chain containing CDR3 (hereinafter referred as "βCDR3 polynucleotide") of TCR of CD4$^+$ helper T-cell clones specific to a WT1 helper peptide. Thus, in one aspect, the present invention provides αCDR3 polynucleotides having nucleotide sequences shown in FIG. 1 (nucleotide sequences selected from the group consisting of SEQ ID NOs: 1, 3, 5, 8, 10, 11, 13, 14, 16, 18, 20, 22, 23, 25, 27, 28, 30, 31, 33, 35, 37, 39, 41, 43, 45, 47, 49, 51, 53, 55, 56, 58), and βCDR3 polynucleotides having nucleotide sequences shown in FIG. 1 (nucleotide sequences selected from the group consisting of SEQ ID NOs: 2, 4, 6, 7, 9, 12, 15, 17, 19, 21, 24, 26, 29, 32, 34, 36, 38, 40, 42, 44, 46, 48, 50, 52, 54, 57, 59).

Figure 1A:
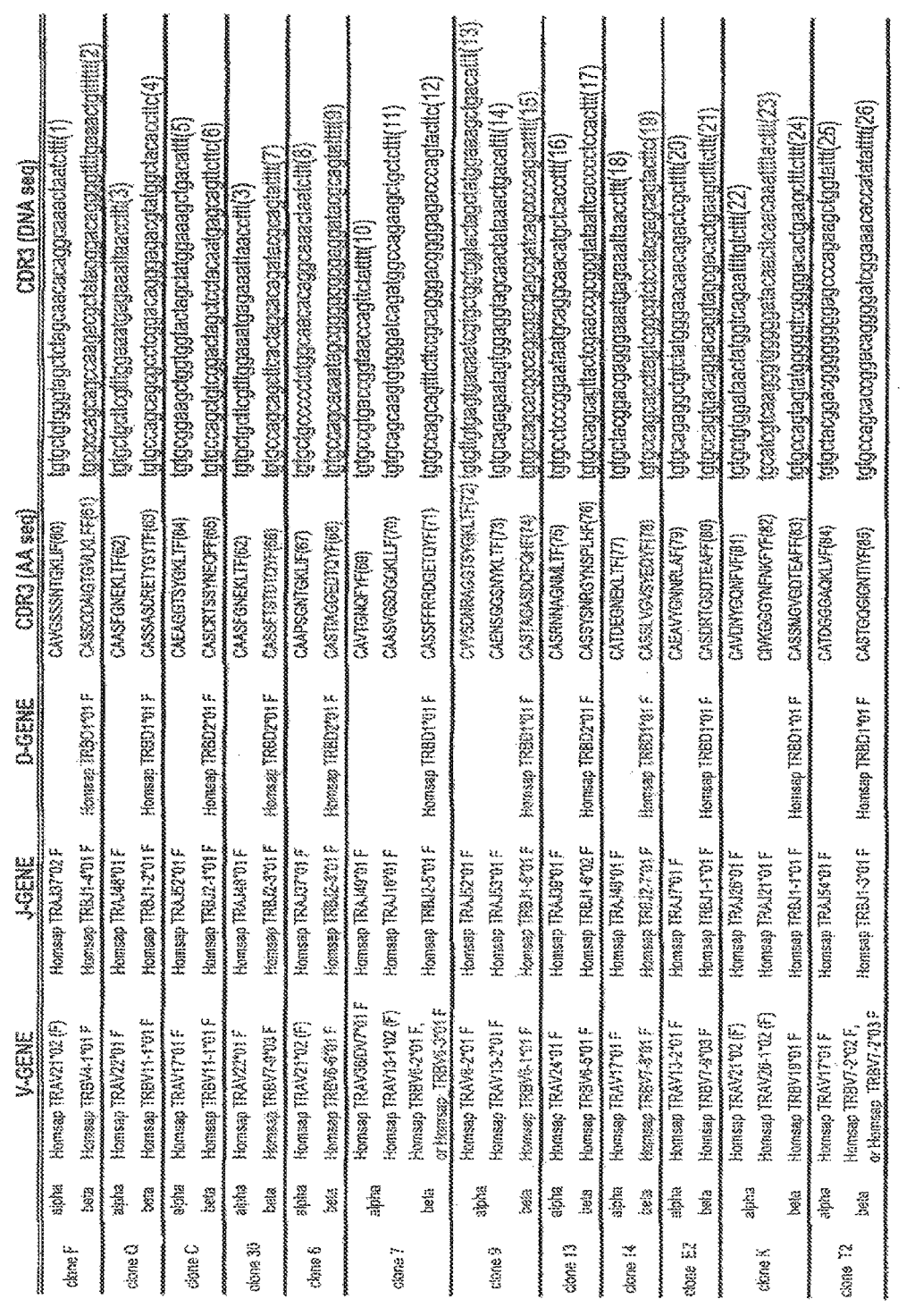
Figure 1B:
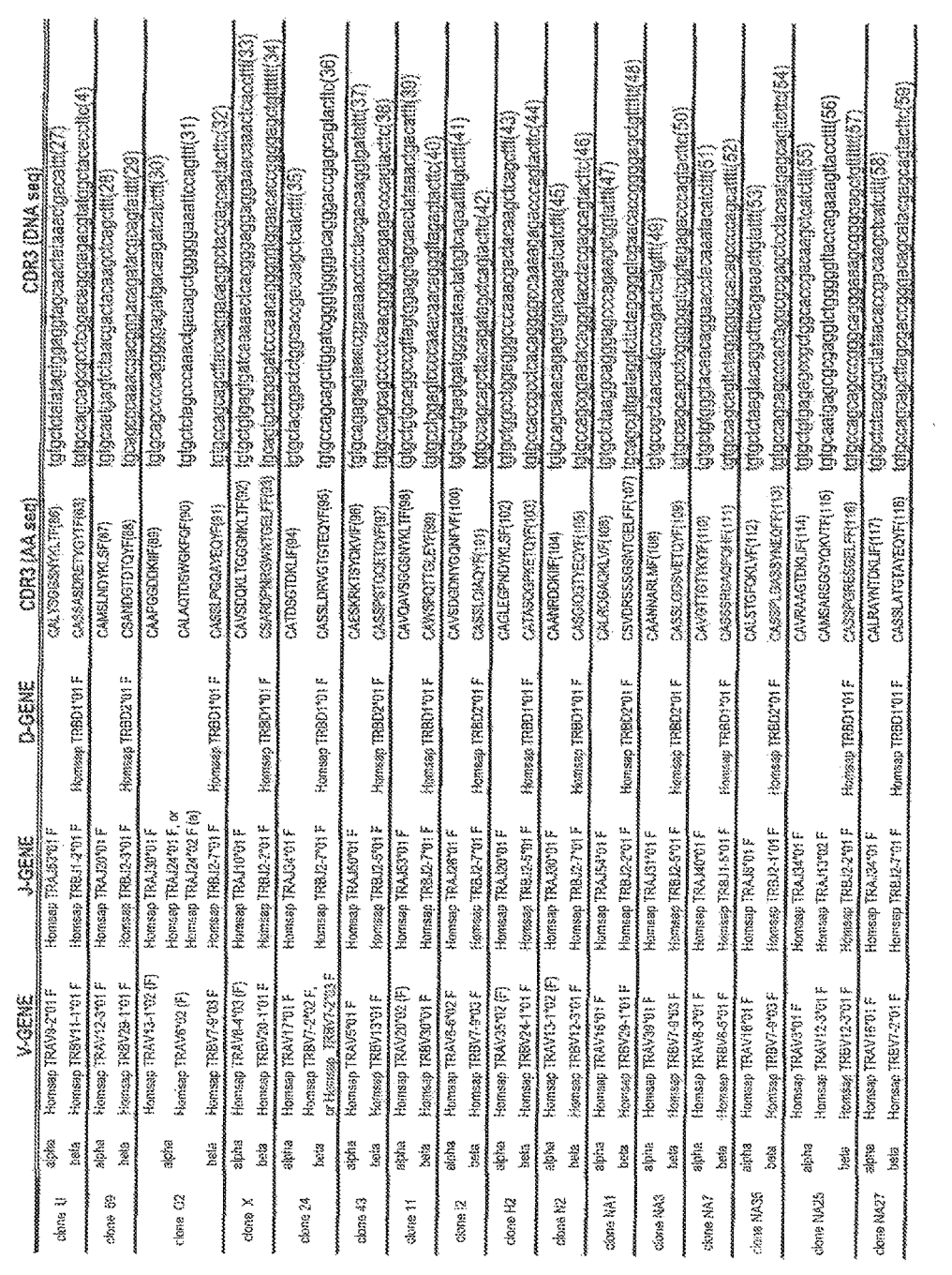

Preferably, from the viewpoint of expression of receptor function, an αCDR3 polynucleotide and a βCDR3 polynucleotide contained in each clone are contained in one TCR. That is, it is preferable that an αCDR3 polynucleotide and a βCDR3 polynucleotide corresponding to each clone form a pair as shown in FIG. 1. Therefore, in a further aspect, the present invention provides a pair of a αCDR3 polynucleotide and a βCDR3 polynucleotide, wherein each polynucleotide constituting the pair has a nucleotide sequence shown in FIG. 1. Combination of a αCDR3 polynucleotide and a βCDR3 polynucleotide differs according to each clone. The nucleotide sequence of a pair of an αCDR3 polynucleotide and a βCDR3 polynucleotide in each clone are as shown in FIG. 1.

A polynucleotide having a nucleotide sequence complementary to a αCDR3 polynucleotide or a βCDR3 polynucleotide is also included in a αCDR3 polynucleotide or a βCDR3 polynucleotide. In addition, a degenerate sequence of a αCDR3 polynucleotide or a βCDR3 polynucleotide is also included in a αCDR3 polynucleotide or a βCDR3 polynucleotide so long as it encodes the peptide shown in FIG. 1.

A polynucleotide having a nucleotide sequence identity of 70% or more, for example 75% or more, 80% or more, 85% or more, or 90% or more, for example 92% or more, 94% or more, 96% or more, or 98% or more, to that of a αCDR3 polynucleotide, is also included in a αCDR3 polynucleotide. A polynucleotide having a nucleotide sequence identity of 70% or more, for example 75% or more, 80% or more, 85% or more, or 90% or more, for example 92% or more, 94% or more, 96% or more, or 98% or more, to that of a βCDR3 polynucleotide, is also included in a βCDR3 polynucleotide.

A polynucleotide having a nucleotide sequence hybridizing to a nucleotide sequence of a αCDR3 polynucleotide under a stringent condition is also included in a αCDR3 polynucleotide. A polynucleotide having a nucleotide sequence hybridizing to a nucleotide sequence of a βCDR3 polynucleotide under a stringent condition is also included in a βCDR3 polynucleotide.

Examples of stringent hybridization conditions include a condition where hybridization is performed in a solution containing 5×SSC, 7% (w/v) SDS, 100 kg/ml denatured salmon sperm DNA and 5×Denhardt' solution at 48-52° C., and then washing is performed in 0.1×SSC, 0.5×SSC, 1×SSC or 2×SSC; or a condition where hybridization is performed in a solution containing 250 mM NaCl, 25 mM trisodium citrate, 1% SDS, 50% formamide and 200 μg/ml denatured salmon sperm DNA at 42° C., and then washing is performed in a solution containing 15 mM NaCl, 1.5 mM trisodium citrate and 0.1% SDS.

In another aspect, the present invention provides peptides encoded by αCDR3 polynucleotides and βCDR3 polynucleotides (referred as "αCDR3 peptide" and "βCDR3 peptide", respectively). These peptides have the amino acid sequences shown in FIG. 1. Preferably, these peptides form a pair of a αCDR3 peptide and a βCDR3 peptide corresponding to each clone as shown in FIG. 1.

In the present specification, an amino acid sequence of a peptide is expressed by conventional one-letter system or three-letter system.

A peptide encoded by variants of a αCDR3 polynucleotide or a βCDR3 polynucleotide is also included in αCDR3 peptide or βCDR3 peptide. A peptide having an amino acid sequence identity of 70% or more, for example 75% or more, 80% or more, 85% or more, or 90% or more, for example 92% or more, or 94% or more, to that of a αCDR3 peptide, is also included in a αCDR3 peptide. A peptide having an amino acid sequence identity of 70% or more, for example 75% or more, 80% or more, 85% or more, or 90% or more, for example 92% or more, or 94% or more, to that of a βCDR3 peptide, is also included in a βCDR3 peptide. In addition, a peptide having an amino acid sequence of a αCDR3 peptide in which one to several (for example, one, two, three, four or five) amino acids are substituted, deleted or added is also included in a αCDR3 peptide; and a peptide having an amino acid sequence of a βCDR3 peptide in which one to several (for example, one, two, three, four or five) amino acids are substituted, deleted or added is also included in a βCDR3 peptide. It is noted that these variant peptides has similar properties to those of the original αCDR3 peptides or βCDR3 peptides.

These polynucleotides and polypeptides can be prepared using chemical methods and/or biological methods well-known in the art.

In the present invention, the WT1 helper peptide is a peptide having an amino acid sequence shown in SEQ ID NO: 123 (Lys Arg Tyr Phe Lys Leu Ser His Leu Gln Met His Ser Arg Lys His) or a variant amino acid sequence thereof (These peptides are referred as "WT1$_{332}$ peptide"). WT1$_{332}$ peptide may have a partial sequence or a variant sequence of WT1 polypeptide. A peptide consisting of an amino acid sequence shown in SEQ ID NO: 123 or a variant sequence thereof is an example of such a peptide.

It is known that WT1$_{332}$ peptide has an ability to bind to a HLA-DRB1*15:01 molecule, a HLA-DPB1*09:01 molecule, HLA-DPB1*05:01 molecule, HLA-DRB1*04:05 molecule or a HLA-DRB1*15:02 molecule.

A variant sequence of the amino acid sequence shown in SEQ ID NO: 123 as above mentioned refers to an amino acid sequence shown in SEQ ID NO: 123 in which one to several (for example, one, two, three, four or five) amino acids are substituted, deleted or added. Or, a variant sequence of the amino acid sequence shown in SEQ ID NO: 123 as above mentioned refers to an amino acid sequence having an identity of 70% or more, for example 75% or more, 80% or more, 85% or more, or 90% or more, to the amino acid sequence shown in SEQ ID NO: 123. Preferably, a peptide having the amino acid sequence shown in SEQ ID NO: 123 or a variant sequence thereof has a length of 25 amino acids or less. A peptide having a variant sequence of the amino acid sequence shown in SEQ ID NO: 123 has similar properties to those of the peptide having the amino acid sequence shown in SEQ ID NO: 123.

In a further aspect, the present invention relates to a TCR gene containing a αCDR3 polynucleotide and a βCDR3 polynucleotide belonging to any pair shown in FIG. 1. Such a TCR gene may be isolated from a CD4+ T-cell specific to WT1$_{332}$ peptide, or may be prepared using well-known genetic engineering technology.

In a further aspect, the present invention relates to a CD4+ helper T-cell (referred as "TCR gene introduced CD4+ helper T-cell") obtained by introducing a TCR gene containing a αCDR3 polynucleotide and a αCDR3 polynucleotide belonging to any pair shown in FIG. 1 into a CD4+ T-cell. A TCR gene introduced CD4+ helper T-cell shows WT1$_{332}$-specific and HLA class II-restricted proliferation and cytokine production.

A skilled person in the art can easily introduce a TCR gene containing a αCDR3 polynucleotide and a αCDR3 polynucleotide belonging to any one of pairs shown in FIG. 1 into a CD4+ T-cell. For example, the introduction of a TCR gene can be done using various kinds of vectors, electroporation, or a gene gun, etc. A TCR gene to be introduced can be modified for the purpose such as improvement of TCR expression efficiency.

Therefore, in a further aspect, the present invention provides a vector containing a TCR gene containing a αCDR3 polynucleotide and a βCDR3 polynucleotide belonging to any pair shown in FIG. 1.

Introduction of a TCR gene may be done by inserting a α-chain gene containing a αCDR3 polynucleotide and a 1-chain gene containing a βCDR3 polynucleotide into individual vectors, and introducing these vectors into a CD4+ T-cell.

Examples of CD4+ T-cells into which a TCR gene containing a αCDR3 polynucleotide and a βCDR3 polynucleotide is introduced include CD4+ T-cells derived from a HLA-DRB1*15:01-positive subject, a HLA-DPB1*09:01-positive subject, a HLA-DPB1*05:01-positive subject, a HLA-DRB1*04:05-positive subject or a HLA-DRB1*15:02-positive subject, but not limited to them. In addition, CD4+ T-cells may be derived from a subject having a cancer, may be derived from a subject having no cancer (a healthy subject), or may be derived from a donor for bone marrow transplantation.

In further aspect, the present invention also relates to a $WT1_{332}$-specific CD4+ helper T-cell comprising a TCR gene containing a αCDR3 polynucleotide and a βCDR3 polynucleotide belonging to any pair shown in FIG. 1.

Induction of a WT1-specific CTL can be enhanced using a TCR gene-introduced CD4+ helper T-cell. Particularly, induction of WT-specific CTL can be enhanced by co-culturing a TCR gene-introduced CD4+ helper T-cell and a peripheral mononuclear cell. Therefore, in further aspect, the present invention provides a method for enhancing the induction of a WT1-specific CTL, comprising co-culturing a TCR gene-introduced CD4+ helper T-cell and a peripheral mononuclear cell. In another aspect, the present invention relates to a WT1-specific CTL obtainable by said method.

Methods and conditions for co-culturing a TCR gene-introduced CD4+ helper T-cell and a peripheral mononuclear cell are well known in the art. Such methods can be performed either in vivo or in vitro. One kind of a TCR gene-introduced CD4+ helper T-cell may be used for enhancing the induction of a WT1-specific CTL. However, preferably two or more kinds of TCR gene-introduced CD4+ helper T-cells are used.

Examples of peripheral mononuclear cells used in the method for enhancing the induction of WT1-specific CTLs of the present invention include peripheral mononuclear cells derived from a HLA-DRB1*15:01-positive subject, a HLA-DPB1*09:01-positive subject, a HLA-DPB1*05:01-positive subject, a HLA-DRB1*04:05-positive subject or a HLA-DRB1*15:02-positive subject, but not limited to them. Preferably, the peripheral mononuclear cells and the CD4+ T-cells are those which have been obtained from a subject in which a cancer should be treated or prevented.

In the co-cultivation, it is preferable that $WT1_{332}$ peptide and/or other WT1 peptides co-exist. Examples of other WT1 peptides include those which have ability to bind to a HLA-DRB*15:01 molecule, a HLA-DPB1*09:01 molecule, a HLA-DPB1*05:01 molecule, a HLA-DRB1*04:05 molecule or a HLA-DRB1*15:02 molecule, but not limited to them.

If necessary, the WT1-specific CTLs obtained by the method mentioned above may be further cultured to make the cell numbers increase, and then administrated to a subject, in order to treat or prevent a cancer in the subject. In such a treatment or prevention of a cancer, it is preferable to co-administrate $WT1_{332}$ peptide and/or other WT1 peptides. By the action of the WT1-specific CTL, CTLs specific to other cancer antigens can also be induced.

A TCR gene-introduced CD4+ helper T-cell can damage cancer cells expressing WT1. Therefore, in further aspect, the present invention is a method for the treatment or prevention of a cancer in a subject, comprising introducing a TCR gene-introduced CD4+ helper T-cell into the subject.

In further aspect, the present invention provides a pharmaceutical composition comprising a TCR gene-introduced CD4+ helper T-cell for the treatment or prevention of a cancer, a use of a TCR gene-introduced CD4+ helper T-cell for the manufacture of a medicament for the treatment or prevention of a cancer, and a use of a TCR gene-introduced CD4+ helper T-cell for the treatment or prevention of a cancer.

As used herein, "treatment" of a cancer refers not only to the treatment of a cancer such as the inhibition of progress of a cancer, the reduction of a cancer and the destruction of a cancer, but also to the prevention of recurrence of a cancer.

Examples of subjects in which a cancer is treated or prevented include a HLA-DRB1*15:01-positive subject, a HLA-DPB1*09:01-positive subject, a HLA-DPB1*05:01-positive subject, a HLA-DRB1*04:05-positive subject or a HLA-DRB1*15:02-positive subject, but not limited to them. The above subject is not limited to a cancer patient, and may be a person not having a cancer (including a healthy person), or may be a donor for bone marrow transplantation.

Embodiments of the method for the treatment or prevention, the pharmaceutical composition, and the use as mentioned above are described below. However, the embodiments are not limited to those. First, CD4+ T-cells are taken from a peripheral blood of a cancer patient who needs a treatment, and a TCR gene containing a αCDR3 polynucleotide and a βCDR3 polynucleotide is introduced into the CD4+ T-cells to obtain TCR gene-introduced CD4+ helper T-cells. The TCR gene-introduced CD4+ helper T-cells thus obtained are administered to the cancer patient. Before the administration, the TCR gene-introduced CD4+ helper T-cells can be cultured and proliferated under appropriate conditions to obtain a sufficient number of cells, and then they can be administered to the cancer patient.

Either one kind of TCR gene-introduced CD4+ helper T-cell or two or more kinds of TCR gene-introduced CD4+ helper T-cells may be administered. From the viewpoint of improvement of treatment or prevention effect, it is preferable that two or more kinds of TCR gene-introduced CD4+ helper T-cells are administered to a subject.

In case that TCR gene-introduced CD4+ helper T-cells are administered to a subject, a physician can appropriately decide conditions such as the number of cells to be administered, the frequency of the administration, the interval of the administration. For example, TCR gene-introduced CD4+ helper T-cells may be administered only once, or administered separately several times. Typically, in case of an adult subject, the number of the TCR gene-introduced CD4+ helper T-cells per dose is in a range between about $10^9$ and about $10^{11}$, but not limited these numbers.

In the treatment or prevention method, the pharmaceutical composition and the use described above, it is preferable that $WT1_{332}$ peptide and/or other WT1 peptides are co-administered. A physician can appropriately decide amount and frequency of administration of $WT1_{332}$ peptide and/or other WT1 peptides. In addition, other anti-cancer therapies or preventions may be combined.

The method for the treatment or prevention, the pharmaceutical composition, and the use described above can be applied to various kinds of cancers, but not limited to, for example, hematologic malignancies, such as acute myelocytic leukemia, acute lymphocytic leukemia, malignant lymphoma, multiple myeloma, chronic myelocytic leukemia, myelodysplastic syndrome, and recurrence after the hematopoietic stem cell transplantation of the same type; solid cancers, such as tongue cancer, gingival cancer, mouth floor cancer, pharyngeal cancer, larynx cancer, salivary gland cancer, and thyroid cancer; thoracic cancers, such as breast cancer, lung cancer, and thymic cancer; gastrointestinal cancers, such as colon cancer, small intestine cancer, gastric cancer, pancreatic cancer, liver cancer, bile duct cancer, gastrointestinal endocrine tumor, and gastrointestinal carcinoid; cancers of urinary and genital tract, such as renal cancer, urothelial cancer, germinoma, Wilms' tumor, prostate cancer, uterine body cancer, cervical cancer, uterine sarcoma, and ovarian malignancy; musculoskeletal malignancies, such as primary malignancy of bone (e.g., osteosarcoma and Ewing's sarcoma) and soft tissue sarcoma; and other cancers, such as skin cancer, neuroblastoma, malignant glioma (glioblastoma), primary malignant lymphoma of the central nervous system, medulloblastoma, and PNET.

The CDR3 regions are the most diverse portions and are the most responsible parts for the specificity of antigen recognition. Thus, the sequences of the αCDR3 polynucleotides, the βCDR3 polynucleotides, the αCDR3 peptides, and the βCDR3 peptides of the present invention are considered peculiar to the CD4$^+$ helper T-cells specific to WT1$_{332}$ peptide. Therefore, in case that a polynucleotide encoding a CDR region of a α-chain and a β-chain, or a peptide corresponding to the CDR region have the sequence of the polynucleotide or the peptide of the present invention, the CD4$^+$ helper T-cell is considered to be specific to WT1$_{332}$ peptide.

For example, (i) a DNA chip comprising one or more kinds of αCDR3 polynucleotides, (ii) a DNA chip comprising one or more kinds of βCDR3 polynucleotides, or (iii) a DNA chip comprising both one or more kinds of αCDR3 polynucleotides and one or more kinds of βCDR3 polynucleotides can be used to measure the frequency of CD4$^+$ helper T-cells specific to WT1$_{332}$ peptide in a sample. Particularly, a sample is prepared by lysing cells in a specimen obtained from a subject and extracting nucleic acids, and the sample is contacted with the DNA chip.

For example, in case that a sample is contacted with the chip (i), and hybridization is found at any position, the same sample is contacted with the chip (ii) to confirm whether hybridization is found or not. Then, in case that any hybridization in the chip (i) and any hybridization in the chip (ii) occur with any αCDR3 polynucleotide and any βCDR3 polynucleotide which constitute any pair shown in FIG. 1, it can be judged that a CD4$^+$ helper T-cell specific to WT1$_{332}$ peptide having a functional TCR exists in the sample. Using the chip (III), the above process can be done in one step.

A DNA chip may be in any form such as a microchip and a microarray. These chips can be prepared by a well-known method. For example, αCDR3 polynucleotides and βCDR3 polynucleotides can be immobilized on a glass substrate by a well-known method. It is preferable that a label which can indicate presence or absence of hybridization and amount of the hybridization is attached to DNAs in a sample or DNA sequences on a chip.

Not only a DNA chip but also techniques such as southern blotting, northern blotting, colony hybridization can be used to measure frequency of CD4$^+$ helper T-cells specific to WT1$_{332}$ peptide in a sample.

In addition, a αCDR3 peptide and a βCDR3 peptide can be used to obtain an antibody to a CD4$^+$ helper T-cell specific to WT1$_{332}$ peptide. A CD4$^+$ helper T-cell specific to WT1$_{332}$ peptide can be detected using such an antibody. A receptor of a CD4$^+$ helper T-cell specific to WT1$_{332}$ peptide can also be stimulated using such an antibody. Such stimulation can be done either in vivo or in vitro.

A chip comprising αCDR3 peptides, a chip comprising αCDR3 peptides, or a chip comprising both αCDR3 peptides and βCDR3 peptides can also be used to detect an antibody to a CD4$^+$ helper T-cell specific to WT1$_{332}$ peptide.

A chip comprising these peptides can be prepared using a well-known method. It is preferable to add a label which can determine presence or absence of a specific binding to peptides in a sample or peptides on a chip.

A chip comprising antibodies to αCDR3 peptides and/or βCDR3 peptides can also be used to determine kind and amount of αCDR3 peptides and/or βCDR3 peptides in a sample, or to determine kind and amount of CD4$^+$ helper T-cells specific to WT1$_{332}$ peptide in a sample.

A chip to which these antibodies are immobilized can be prepared using a well-known method. It is preferable to add a label which can determine presence or absence of a specific binding to peptides in a sample or antibodies on a chip.

DESCRIPTION OF SEQUENCES

SEQ ID NOs: 1 to 59 are nucleotide sequences encoding CDR3 contained in TCR of CD4$^+$ helper T-cell clones.
SEQ ID NOs: 60 to 118 are amino acid sequences of CDR3 contained in TCR of CD4$^+$ helper T-cell clones.
SEQ ID NO: 119 is a reverse primer for amplifying TCRα chain.
SEQ ID NO: 120 is a reverse primer for amplifying TCRβ chain.
SEQ ID NO: 121 is a reverse primer for amplifying TCRβ chain.
SEQ ID NO: 122 is a primer for determining CDR3 nucleotide sequences.
SEQ ID NO: 123 is an amino acid sequence of WT1$_{332}$ peptide.
SEQ ID NO: 124 is an amino acid sequence of HIV peptide.
SEQ ID NO: 125 is an amino acid sequence of a variant of a naturally occurring WT1 peptide.

The present invention is described more particularly and more concretely by showing examples below. However, it should not be construed that examples limit the scope of the present invention.

Example 1

Example 1 Establishment of WT1$_{332}$-Specific CD4$^+$ T-Cell Clones and Isolation and Sequencing of T-Cell Receptor (TCR) Genes The experimental procedures were as follows.
(1) Method of Establishing WT1$_{332}$-Specific CD4$^+$ T-Cell Clones
(i) Peripheral blood mononuclear cells (PBMCs) derived from a healthy subject are harvested and seeded into 24-well plates at 3×10$^6$ cells/well. X-VIVO 15 medium supplemented with 10% AB serum and 40 IU/ml IL-2 is used as a medium.
(ii) WT1$_{332}$ peptide is added to the above i at a final concentration of 20 µg/ml and the cells are cultured for 7 days.

(iii) After 7 days, the cells are collected and prepared with X-VIVO 15 medium supplemented with 10% AB serum so that the cell density is 1×107 cells/ml, and then, seeded by 100 μL each into 96 well, round bottom plates.

(iv) WT1$_{332}$ peptide, BD GolgiStop™ (BD Bioscience) and CD28/CD49d Costimulatory Reagent (BD Bioscience) are added to X-VIVO 15 medium supplemented with 10% AB serum at final concentrations of 40 μg/ml, 4 μg/ml, and 4 μg/ml, respectively.

(v) The above iv is added by 100 μL each to the above iii.

(vi) Anti-human CD154-APC-labeled antibody (BD Bioscience) is added by 10 μl each to the above v and the plates are incubated in 5% $CO_2$ incubator for 6 hours at 37° C.

(vii) After incubation, the cells are collected and stained with anti-human CD4-APC-H7-labeled antibody (BD Bioscience) and anti-human CD3-Pacific Blue-labeled antibody (BD Bioscience) as well as 7-AAD (eBioscience) for removing dead cells.

(viii) PBMCs are harvested from 3 healthy subjects, mixed, irradiated with 30 Gy of γ-ray, and prepared with X-VIVO 15 medium supplemented with 10% AB serum at a final concentration of 10%, IL-2 at a final concentration of 100 IU/ml, and PHA at a final concentration of 3 μg/ml so that the cell density is 1×106 cells/ml. These prepared cells are seeded by 100 μL each into 96 well, round bottom plates.

(ix) 7-ADD-CD3$^+$CD4$^+$CD154$^+$ cell fraction, i.e., a fraction containing WT1$_{332}$-specific CD4$^+$ T-cells is single-cell sorted into each well of the above viii using FACSAria cell sorter.

(x) After culture for 10-14 days, the proliferated cells in each well are used as independent CD4$^+$ T-cell clones.

(2) Screening of WT1$_{332}$-Specific CD4$^+$ T-Cell Clones (i) Each CD4$^+$ T-cell clone of the above (1)-x is prepared with X-VIVO 15 medium supplemented with 1% AB serum so that the cell density is 3×105 cells/ml.

(ii) Autologous PBMCs pulsed with WT1$_{332}$ or not pulsed with any peptides are irradiated with 30 Gy of γ-ray and prepared with X-VIVO 15 medium supplemented with 1% AB serum so that the cell density is 1×106 cells/mi.

(iii) The above (2)-i and ii are seeded by 100 μL each into 96 well, round bottom plates.

(iv) After culture for 2 days, 3H-thymidine is added to each well at 1 μCi/well.

(v) After 18 hours, the 3H-thymidine incorporated into each CD4$^+$ T-cell clone is measured and the CD4$^+$ T-cell clones showing WT1$_{332}$-specific proliferative response are selected. These selected clones are used as WT1$_{332}$-specific CD4$^+$ T-cell clones.

(vi) The culture of the WT1$_{332}$-specific CD4$^+$ T-cell clones is performed with stimulation of the WT1$_{332}$-specific CD4$^+$ T-cell clones by co-culturing with PBMCs that were prepared by irradiating autologous PBMCs pulsed with WT1$_{332}$ at a frequency of once per 1-2 weeks or so with 30 Gy of γ-ray.

(3) Isolation of TCR genes using 5'-RACE (Rapid Amplification of cDNA End) method (i) WT1$_{332}$-specific CD4$^+$ T-cell clones are cultured for 10 days or more from the last stimulation. This is to prevent contamination with T-cells contained in autologous PBMCs that are used for the stimulation.

(ii) The WT1$_{332}$-specific CD4$^+$ T-cell clones are pelleted, TRIzol reagent (Invitrogen) is added thereto, and RNA is extracted according to its manual.

(iii) cDNAs are synthesized from the RNA extracted in the above (3)-ii using SMARTer™ RACE cDNA Amplification Kit (Clontech).

(iv) TCR α-chain and β-chain genes are amplified by using the cDNAs synthesized in the above (3)-iii as templates. In regard to used primers, UPM primer included in MARTer™ RACE cDNA Amplification Kit was used as a forward primer and the following TCR-specific primers were used as reverse primers:

Cα3'UTR-primer: 5'-CAC AGG CTG TCT TAC AAT CTT GCA GAT C-3' (SEQ ID No: 119)

Cβ1-3'UTR-primer: 5'-CTC CAC TTC CAG GGC TGC CTT CA-3' (SEQ ID No: 120)

Cβ2-3'UTR-primer: 5'-TGA CCT GGG ATG GTT TTG GAG CTA-3' (SEQ ID No: 121).

(v) The amplification of the TCR genes was performed using KOD FX available from ToYoBo under conditions of 94° C., 3 min→(98° C., 10 sec→68° C., 1 min)×35 cycles.

(vi) The size of PCR products are confirmed using agarose gel electrophoresis and bands of near 1 kbp are cut from gel and purified.

(vii) After adenines are added to the PCR products purified in the above (3)-vi using Taq polymerase, the resultants are ligated into pCR 2.1 vectors.

(viii) HST02 competent cells are transformed with the above (3)-vii, plasmids are purified from single colonies, and then, sequenced.

(ix) The sequence analysis is performed using the International Immunogenetics Information System (www.imgt.org/IMGT_vquest/vquest?livret=0&Option=humanTcR) and each TCR gene is identified.

With regard to the above (3) "isolation of TCR genes using 5'-RACE (Rapid Amplification of cDNA End) method", the detailed experimental procedure is shown below.

(3-1) RNA Extraction

RNA extraction from T-cell clones was performed using TRIzol Reagent (Invitrogen). As for T-cell clones used, the clones cultured without antigen-stimulation in the presence of IL-2 over 3 weeks were prepared for the purpose of preventing contamination with feeder cells.

(3-2) Cloning of full-length TCR (T-cell receptor) cDNA using 5'-RACE (Rapid Amplification of cDNA Ends) method For cloning of TCR α/β, SMARTer™ RACE cDNA Amplification Kit (Clontech) was used. Firstly, 5'-RACE reaction was performed according to its manual, and thereby 1st strand cDNA was synthesized. Then, in order to obtain full-length TCR α-chain and β-chain cDNAs, PCR reaction was performed by using reverse primers specific to each of 3'UTRs (Untlansrated Regions) and universal primer (UPM) which is included in the kit and using the synthesized 1st strand cDNA as a template. The used primers are as follows.

Cα 3'UTR-RACE-primer: CACAGGCTGTCTTA-CAATCTTGCAGATC (SEQ ID No:119)

Cβ1 3'UTR-RACE-primer: CTCCACTTCCAGGGCT-GCCTTCA (SEQ ID No:120)

Cβ2 3'UTR-RACE-primer: TGACCTGGGATG-GTTTTGGAGCTA (SEQ ID No:121)

Further, PCR reaction was performed in the following reaction solution composition using KOD FX (TOYOBO).

TABLE 1

| 2x PCR buffer for KOD FX | 12.5 μl |
|---|---|
| 2 mM dNTPs | 5.0 μl |
| 10x UPM | 2.5 μl |
| 10 μM reverse primer | 1.0 μl |

TABLE 1-continued

| Template DNA | 1.0 μl |
|---|---|
| KOD FX (1.0 U/μl) | 0.5 μl |
| distilled water | up to 25 μl |
| Volume of the reaction solution | 25 μl |

PCR cycle is as follows: 94° C., 2 min → (98° C., 10 sec → 68° C., 1 min) × 35 cycles → 15° C., hold After the PCR reaction, 1.0% agarose gel electrophoresis was performed, single bands of near 900-1000 bp were cut, and the PCR products were purified with 50 μl of distilled water using QIAquick Gel Extraction Kit (QIAGEN). It is necessary to add adenine to both ends of the PCR products for TA-cloning. The addition of adenine was performed using Platinum Taq DNA polymerase (invitrogen) as follows.

(1) 2× reaction solution shown in the table below is prepared.

TABLE 2

| 10x PCR buffer | 10 μl |
|---|---|
| 2 mM dNTPs | 10 μl |
| 25 mM MgCl2 | 8.0 μl |
| Platinum Taq polymerase | 1.0 μl |

21 μl of distilled water is added so that a total volume is 50 μl.

(2) 2× reaction solution is incubated at 95° C. for 5 minutes.
(3) The purified PCR products are added thereto.
(4) The resultants are incubated at 72° C. for 10 minutes.

PCR products added with adenines were purified and concentrated by ethanol precipitation, and then, inserted into pCR 2.1 vectors (invitrogen) using DNA Ligation Kit, Mighty Mix>(TaKaRa). pCR 2.1 vectors comprising the PCR products were introduced into HST02 competent cells by transformation and cloned.

(3-3) Purification of Plasmids Comprising Full-Length TCR α-Chain and β-Chain cDNAs The transformed HST02 competent cells were plated on ampicillin/LB plates and incubated at 37° C. Then, single colonies were picked into ampicillin/LB liquid medium, and incubated 37° C. while being stirred at 200 rpm. Then, plasmids were purified from the *Escherichia coli* solution using AUTOMATIC DNA ISOLATION SYSTEM PI-50 (KURABO).

(3-4) Determination of CDR3 Sequence of TCR by Sequencing

For sequencing of the purified plasmids, BigDye® Terminator v3.1 Cycle Sequencing Kit (Applied Biosystems) was used. In addition, M13 reverse primer: caggaaacagctatgac (SEQ ID No: 122) was used. For analysis of TCR and CD3, IMGT/V-QUEST (www.imgt.org/IMGT_vquest/share/textes/) was utilized.

The determined nucleotide and amino acid sequences of CDR3 are shown in FIG. 1. In some of the clones, there were 2 kinds of α-chain and 2 kinds of CDR 3 sequences.

Example 2

Example 2 Introduction of T-Cell Receptor (TCR) Genes Derived from a $WT1_{332}$-Specific CD4+ T-Cell to Human CD4+ T-Cells It was confirmed that human CD4+ T-cell transduced with T-cell receptor (TCR) genes derived from a $WT1_{332}$-specific CD4+ T-cell showed proliferative response and production of cytokines in a $WT1_{332}$-specific and HLA class II-restricted manner.

TCR genes shown in Table 3 were isolated from clone 9 which is the CD4+ T-cell clone which specifically recognizes $WT1_{332}$ in an HLA-DPB1*05:01-restricted manner. These TCR genes were transduced into CD4+ T-cells derived from peripheral blood of healthy subjects by using lentivirus vectors, and the response to $WT1_{332}$ was examined by using the productions of cytokines (interferon-γ and IL-2) as indicators (FIGS. 2A and B). In addition, CD4+ T-cells transduced with lentivirus vectors not carrying TCR genes (indicated as mock) were used as a control. CD4+ T-cells transduced with $WT1_{332}$-specific TCR genes (referred as "$WT1_{332}$-TCR-transduced CD4+ T-cells" in the section of Examples) produced INF-γ and IL-2 in response only to $WT1_{332}$, i.e., in a $WT1_{332}$-specific manner. On the other hand, the mock-transduced CD4+ T-cells did not show $WT1_{332}$-specific production of cytokines.

Figure 2C:
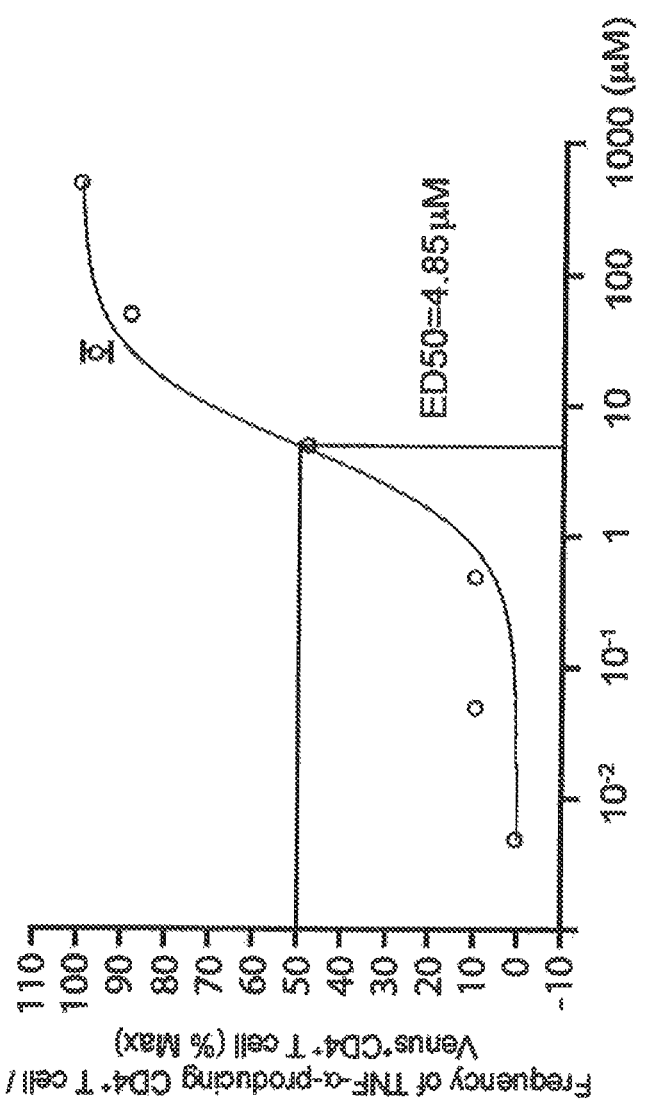
FIG. 2C shows TNF-α production response of WT1$_{332}$-specific CD4$^+$ helper T-cells into which TCR genes have been introduced, to WT1$_{332}$ peptide concentration.

The effect of the concentration of $WT1_{332}$ peptide on the expression of cytokine by $WT1_{332}$-TCR-transduced CD4+ T-cells was examined. $WT1_{332}$-TCR-transduced CD4+ T-cells were stimulated with various concentrations of $WT1_{332}$ peptide for 4 hours, and intracellular cytokine staining assay was performed to examine the ratio of TNF-α-producing CD4+ T-cells to CD4+ T-cells. The results are shown in FIG. 2C.

The production of the cytokine was $WT1_{332}$ peptide concentration-dependent and ED50 was 4.85 μM.

Figure 2D:
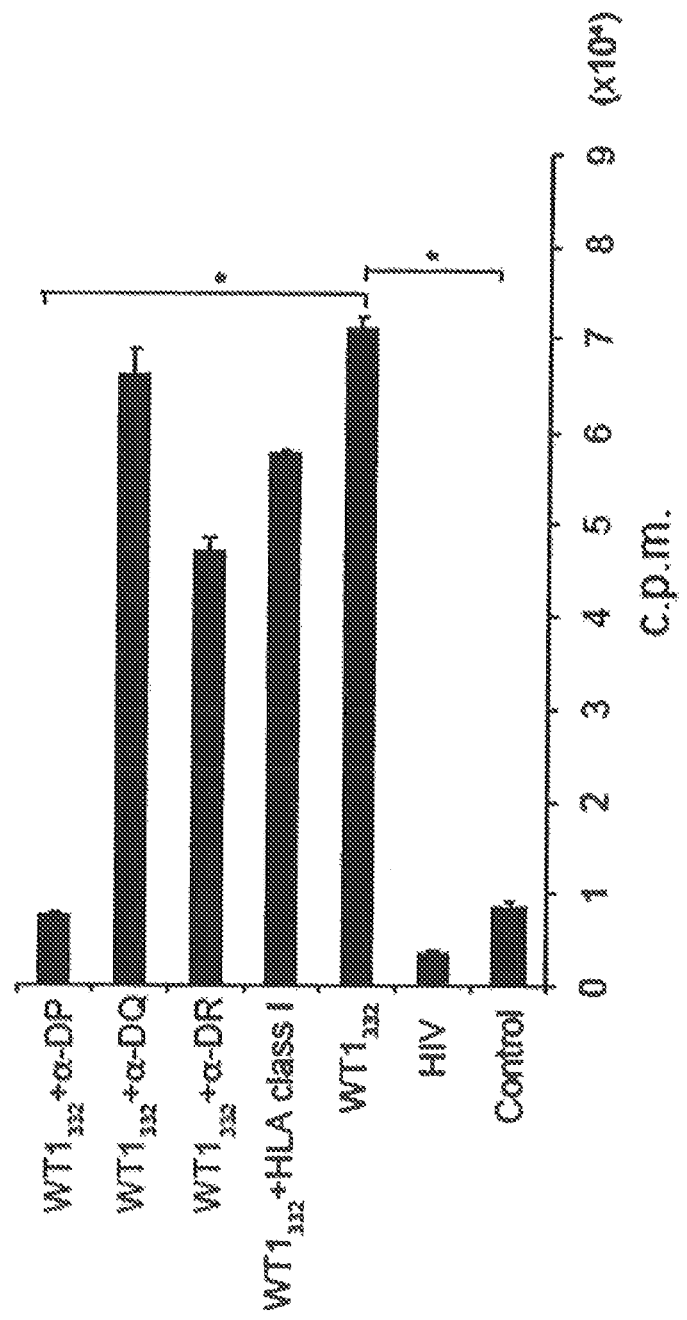
FIG. 2D shows proliferation ability of WT1$_{332}$-specific CD4$^+$ helper T-cells into which TCR genes have been introduced, in systems into which several kinds of substances are added. WT1$_{332}$ represents the culture in the presence of WT1$_{332}$ peptide. α-DP represents the culture in the presence of an anti-HLA-DP antibody. α-DQ represents the culture in the presence of an anti-HLA-DQ antibody. α-DR represents the culture in the presence of an anti-HLA-DR antibody. HLA class I represents the culture in the presence of an anti-HLA class I antibody. HIV represents the culture in the presence of HIV peptide (FRKQNPDIVIY-QYMDDLYVG) (SEQ ID NO: 124).

When a proliferation potency of the $WT1_{332}$-TCR-transduced CD4+ T-cells was examined, a $WT1_{332}$-specific, strong proliferation potency was found and the proliferative response was markedly inhibited by anti-HLA-DP antibody (FIG. 2D).

Figure 2E:
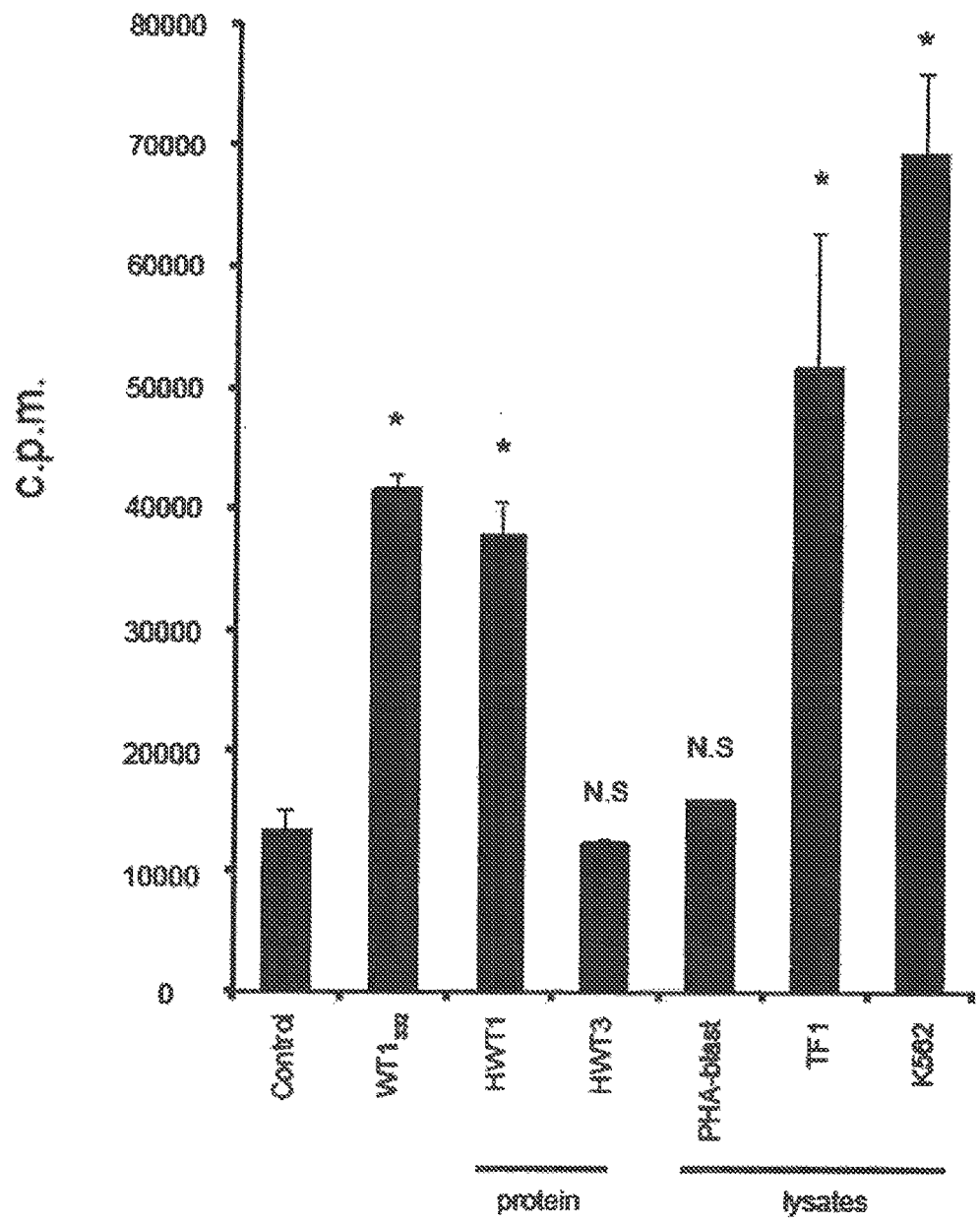
FIG. 2E shows proliferation of WT1$_{332}$-specific CD4$^+$ helper T-cells into which TCR genes have been introduced, in the presence of PBMC pulsed with several kinds of substances. WT1$_{332}$ represents the stimulation by autologous PBMC pulsed with WT1$_{332}$ peptide. HWT1 represents the stimulation by autologous PBMC pulsed with full length of WT1 protein. HWT3 represents the stimulation by autologous PBMC pulsed with truncated WT1 protein (not containing WT1$_{332}$ sequence). PHA-blast represents the stimulation by PBMC pulsed with PHA-blast lysate. TF1 represents the stimulation by PBMC pulsed with a lysate of leukemic cell line TF-1 expressing WT1. K562 represents the stimulation by PBMC pulsed with a lysate of leukemic cell line K562 expressing WT1.
Figure 2F:
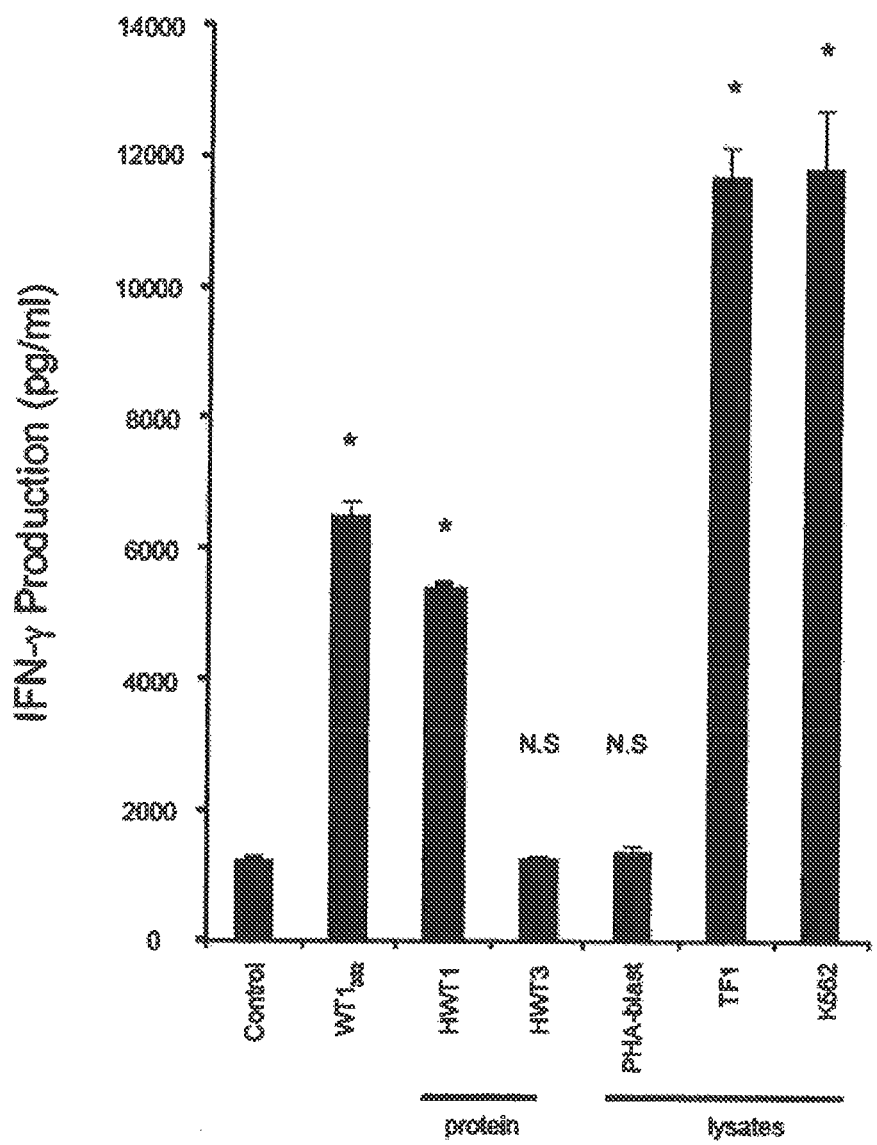
FIG. 2F shows IFN-γ production by WT1$_{332}$-specific CD4$^+$ helper T-cells into which TCR genes have been introduced, in the presence of PBMC pulsed with several kinds of substances. WT1$_{332}$ represents the stimulation by autologous PBMC pulsed with WT1$_{332}$ peptide. HWT1 represents the stimulation by autologous PBMC pulsed with full length of WT1 protein. HWT3 represents the stimulation by autologous PBMC pulsed with truncated WT1 protein (not containing WT1$_{332}$ sequence). PHA-blast represents the stimulation by PBMC pulsed with PHA-blast lysate. TF1 represents the stimulation by PBMC pulsed with a lysate of leukemic cell line TF-1 expressing WT1. K562 represents the stimulation by PBMC pulsed with a lysate of leukemic cell line K562 expressing WT1.

Next, the proliferative response and IFN-γ production of the $WT1_{332}$-TCR-transduced CD4+ T-cells to autologous PBMCs pulsed with $WT1_{332}$ peptide, autologous PBMCs pulsed with full-length WT1 protein, autologous PBMCs pulsed with truncated WT1 protein (not comprising $WT1_{332}$ sequence), PBMCs pulsed with the lysate of PHA-blast, PBMCs pulsed with the lysate of leukemia cell line TF-1 expressing WT1, and PBMCs pulsed with the lysate of leukemia cell line K562 expressing WT1 were examined. The cell proliferation was measured by [3H]-thymidine incorporation, and IFN-γ was measured by ELISA. The results are shown in FIG. 2E and FIG. 2F, respectively. It was found that the proliferation and IFN-γ production of the $WT1_{332}$-TCR-transduced CD4+ T-cells were markedly stimulated by PBMCs pulsed with the lysate of leukemia cell lines (TF-1 and K562) expressing WT1 and also stimulated by autologous PBMCs pulsed with $WT1_{332}$ peptide and autologous PBMCs pulsed with full-length WT1 protein.

Figure 2G:
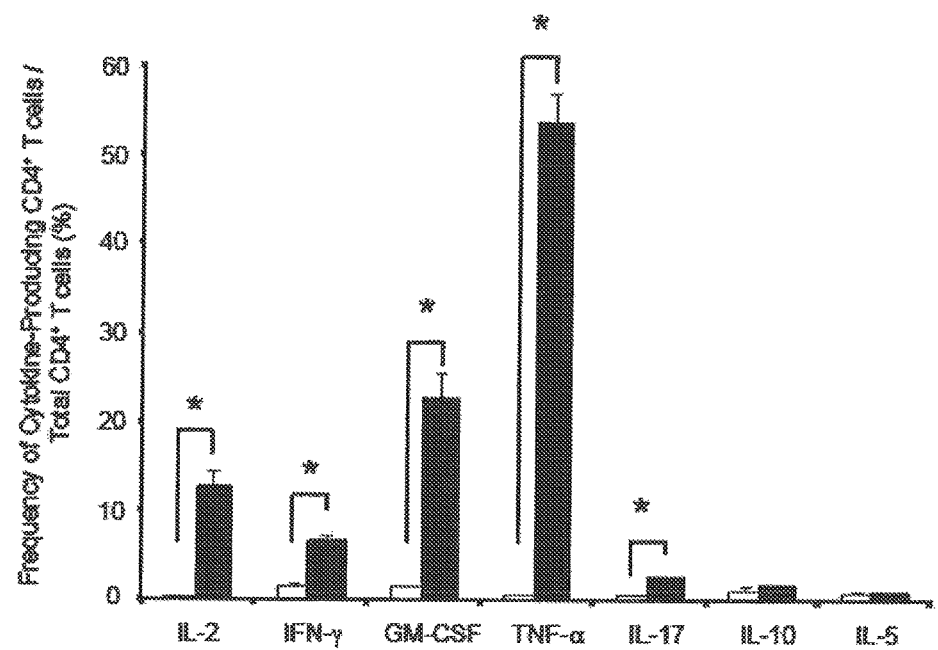
FIG. 2G shows the average of the production of several kinds of cytokines in response to WT1$_{332}$ peptide by WT1$_{332}$-specific CD4$^+$ helper. T-cell lines from three healthy subjects (HLA-DPB1*05:01-positive) into which TCR genes have been introduced. Black bars represent with the stimulation by WT1$_{332}$ peptide. White bars represent without the stimulation.

Further, the production of various cytokines that responded to $WT1_{332}$ peptides of $WT1_{332}$-TCR-transduced CD4+ T-cell lines prepared similarly to those of Example 2, that were derived from 3 healthy (HLA-DPB1*05:01 positive) donors (i.e., three kinds of cell lines), was also examined. The mean values of the cytokine-producing abilities of the three kinds of cell lines are shown in FIG. 2G. Th1-type cytokines such as IL-2, IFN-γ, TNF-α and GM-CSF were produced in large amount.

TABLE 3

TCR genes isolated form clone 9

| | V gene | J segment | D gene | CDR3 sequence |
|---|---|---|---|---|
| Va 8.2 | TRAV13-2*01 | TRAJ53*01 | — | CAENSGGSNYKLTF (SEQ ID No: 73) |
| Vb 13.3 | TRAB6-1*01 | TRBJ1-5*01 | TRBD01*01 | CASTAGASDQPQHF (SEQ ID No: 74) |

Example 3

Example 3 Enhanced Induction of WT1-Specific CTLs by Human CD4+ T-Cells Transduced with TCR Genes Derived from WT1$_{332}$-Specific CD4+ T-Cells Generally, it is known that CD4+ T-cell serves as helper T-cell and is important for introduction and maintenance of CD8+ T-cells (CTLs) that are the primary effector cells that attack cancer cells. Thus, it was examined whether WT1$_{332}$-TCR-transduced CD4+ T-cells enhanced the induction of WT1-specific CTLs.

Figure 3A:
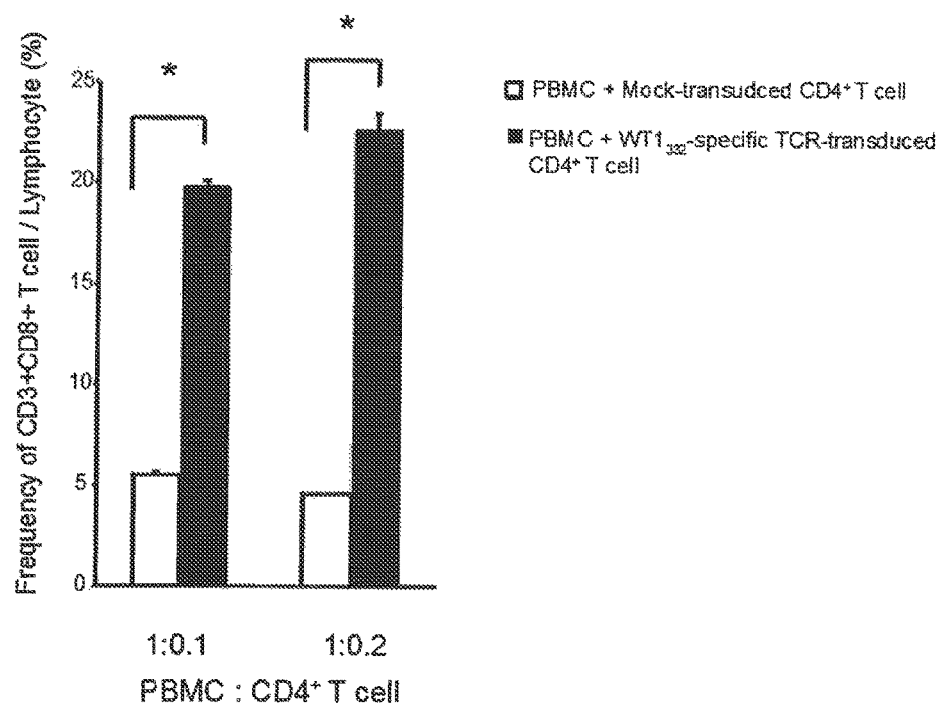
FIG. 3A shows the frequency of CD3$^+$CD8$^+$T cells in case PBMC and WT1$_{332}$-specific CD4$^+$ helper T-cells into which TCR genes have been introduced are co-cultured at the ratio as shown in the figure.
Figure 3B:
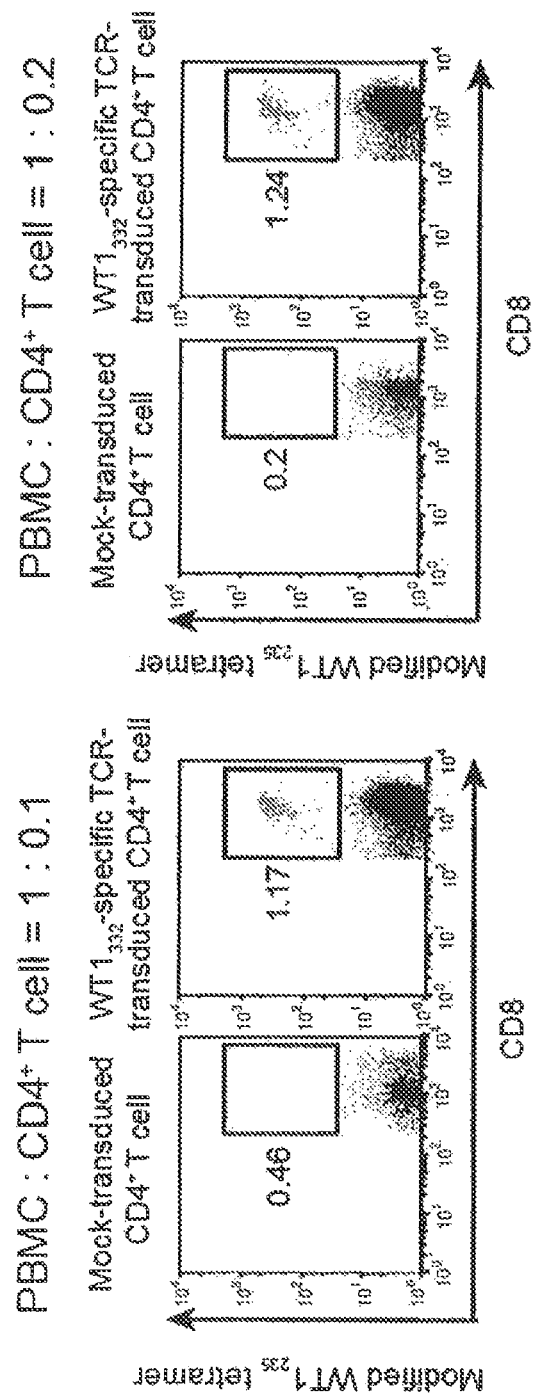
FIG. 3B shows the frequency of the modified WT1$_{235}$/HLA-A*24:02 tetramer-positive CD8*T cells in case PBMC and WT1$_{332}$-specific CD4$^+$ helper T-cells into which TCR genes have been introduced are co-cultured at the ratio as shown in the figure.
Figure 3C:
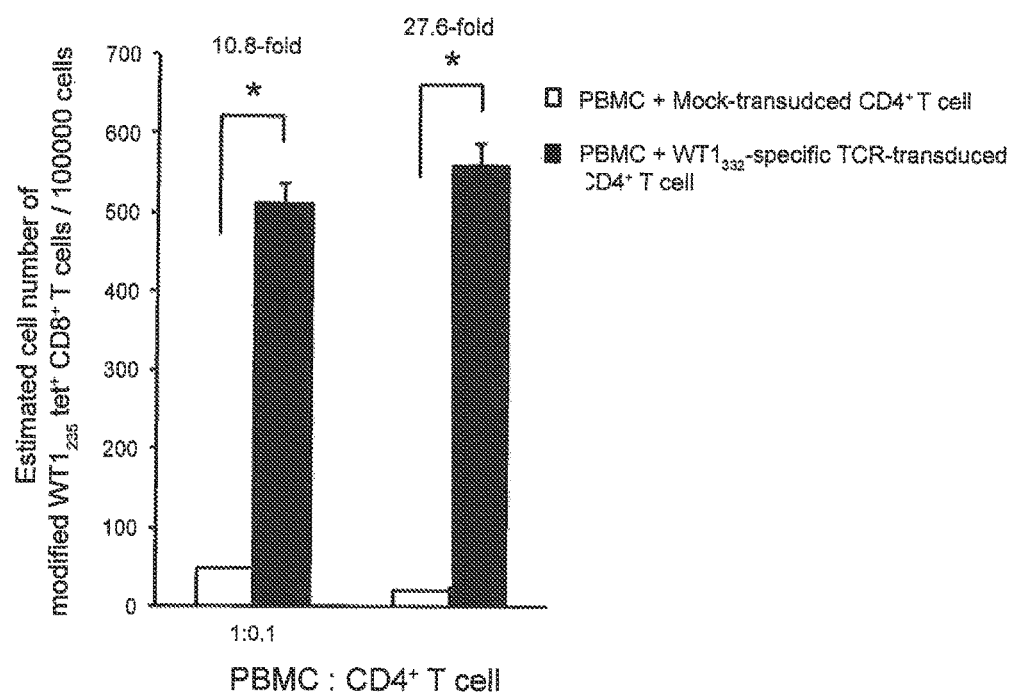
FIG. 3C shows the cell number of WT1-specific CTL in case PBMC and WT1$_{332}$-specific CD4$^+$ helper T-cells into which TCR genes have been introduced are co-cultured at the ratio as shown in the figure.
Figure 3D:
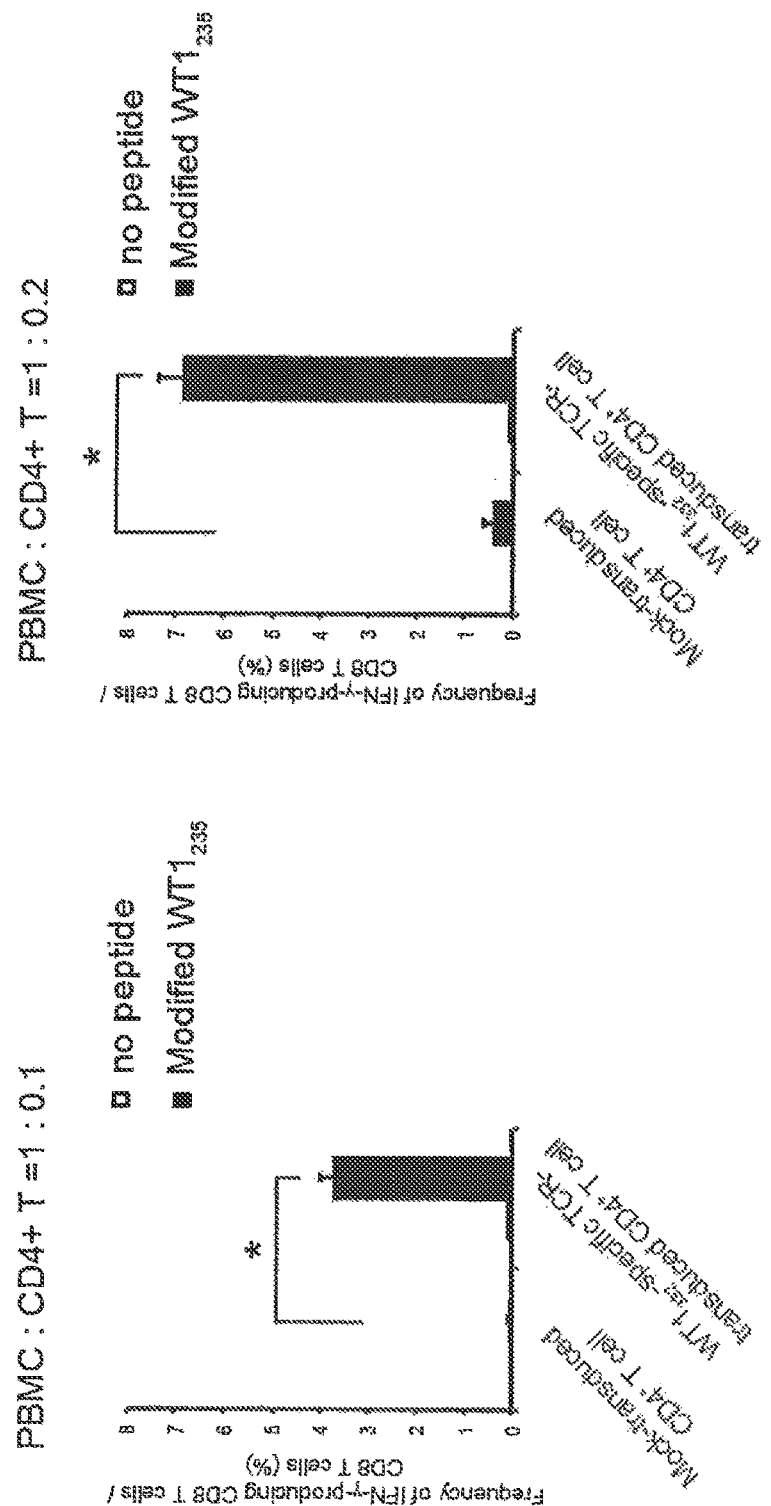
FIG. 3D shows the frequency of CD8$^+$T cells expressing interferon-γ in response to the stimulation by the modified WT1$_{235}$ in case PBMC and WT1$_{332}$-specific CD4$^+$ helper T-cells into which TCR genes have been introduced are co-cultured at the ratio as shown in the figure.

PBMCs of HLA-A*24:02 and HLA-DPB1*05:01-positive healthy subjects were mixed with WT1$_{332}$-TCR-transduced CD4+ T-cells prepared from the same healthy subjects at the ratio of 10:1 and 5:1 (indicated as 1:0.1 and 1:0.2 in FIG. 3) and incubated for 1 week in the presence of a modified WT1$_{235}$ peptide (wherein M, the second amino acid of natural WT1 peptide binding to HLA-A*24:02 molecule, was modified into Y (CYTWNQMNL) (SEQ ID No:125)) that is an HLA-A*24:02-restricted CTL epitope derived from WT1 and WT1$_{332}$. Then, the resultant was stimulated again with the modified WT1$_{235}$ peptide (wherein the binding ability to HLA-A*24:02 molecule were enhanced) and further incubated for 1 week. No IL-2 was added in a series of cultures in order to correctly evaluate the help activity of CD4+ T-cells. After 2 weeks cultures in total, it was examined whether the induction of WT1-specific CTLs was enhanced by the WT1$_{332}$-TCR-transduced CD4+ T-cells by using frequencies of CD8+ T-cells, modified WT1$_{235}$/HLA-A*24:02 tetramer-positive CD8+ T-cells, and modified WT1$_{235}$-specific interferon-γ (INF-γ)-expressing CD8+ T-cells as indicators. As a result, the frequency of CD8+ T-cells was significantly higher when co-cultured with the WT1$_{332}$-TCR-transduced CD4+ T-cells as compared when cultured with the mock-transduced CD4+ T-cells as a control (FIG. 3A). In addition, in regard to the modified WT1$_{235}$/HLA-A*24:02 tetramer positive CD8+ T-cells that are WT1-specific CTLs, a clearly positive population was found when co-cultured with the WT1$_{332}$-TCR-transduced CD4+ T-cells, however, it was not found in the control (FIG. 3B). Calculating the cell number of the WT1-specific CTLs present in 100,000 lymphocytes from these results, the cell number was about 28 times higher when co-cultured with the WT1$_{332}$-TCR-transduced CD4+ T-cells compared with the control (FIG. 3C). Likewise, the frequency of the CD8+ T-cells expressing INF-γ by the stimulation with the modified WT1$_{235}$ was also significantly high when co-cultured with the WT1$_{332}$-TCR-transduced CD4+ T-cells (FIG. 3D). From the above, it was revealed that the WT1$_{332}$-TCR-transduced CD4+ T-cells enhanced the induction of WT1-specific CTLs.

Example 4

Example 4 HLA-DPB1*05:01-Restricted Damage of WT1-Expressing Leukemia Cells by Human CD4+ T-Cells Transduced with TCR Genes Derived from WT1$_{332}$-Specific CD4+ T-Cells Next, the cytotoxic activity, i.e., killing activity, of WT1$_{332}$-TCR-transduced CD4+ T-cells was evaluated.

Figure 4A:
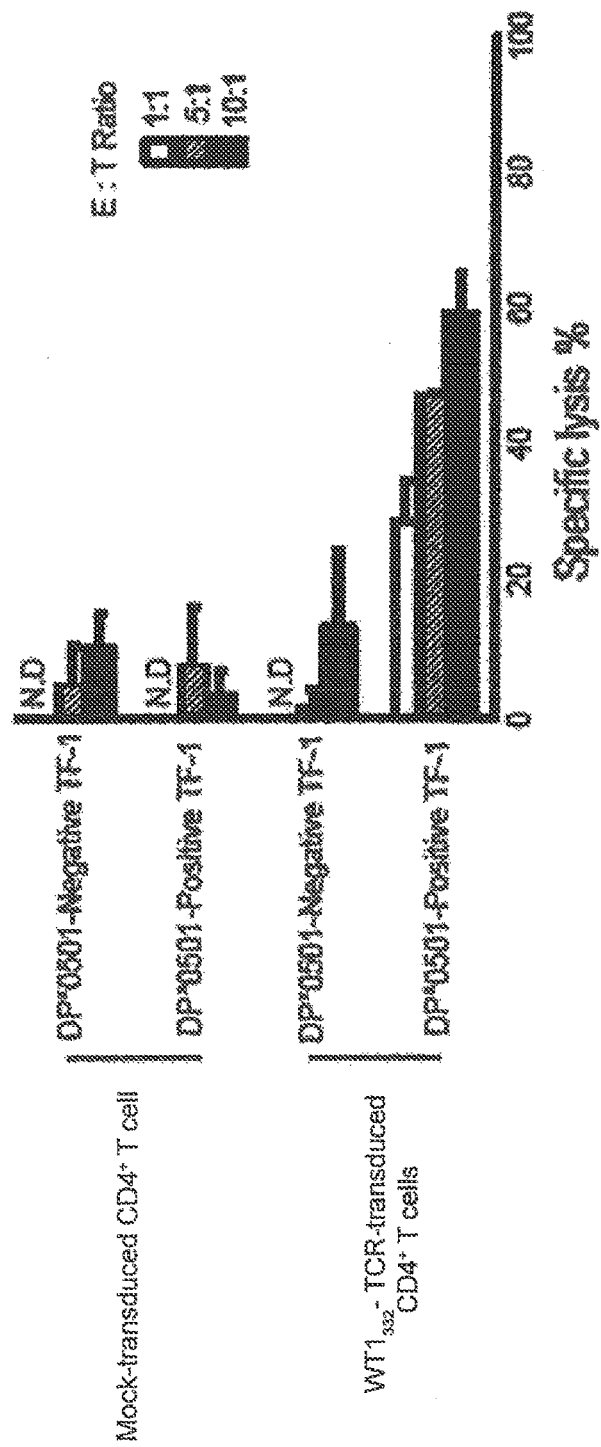
FIG. 4A shows the damage as the lysis (%) of HLA-DPB1*05:01-positive leukemic cell line TF-1 expressing WT1 and HLA-DPB1*05:01-negative leukemic cell line TF-1 expressing WT1 by WT1$_{332}$-specific CD4$^+$ helper T-cells into which TCR genes have been introduced at the E:T ratio as shown in the figure.
Figure 4B:
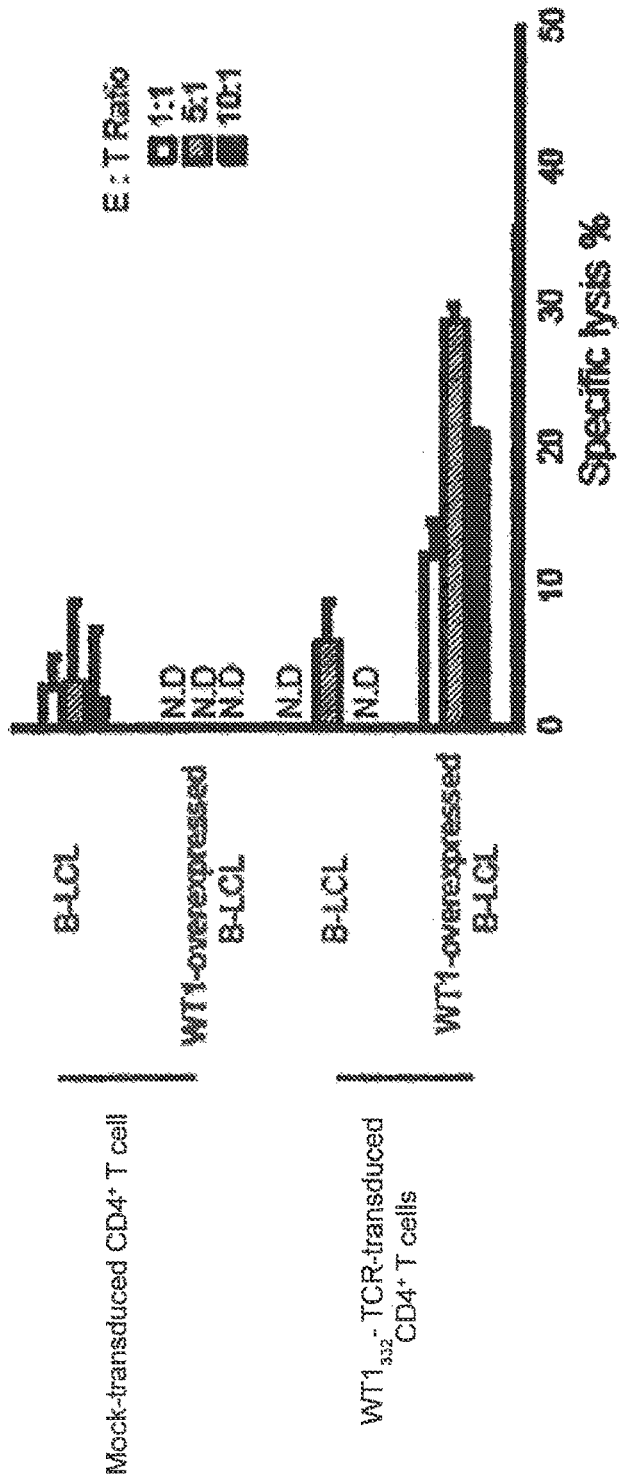
FIG. 4B shows the damage as the lysis (%) of HLA-DPB1*05:01-positive B-LCL cells which have been enforced to express WT1 and HLA-DPB1*05:01-positive B-LCL cells which do not express WT1 by WT1$_{332}$-specific CD4$^+$ helper T-cells into which TCR genes have been introduced at the E:T ratio as shown in the figure.
Figure 4C:
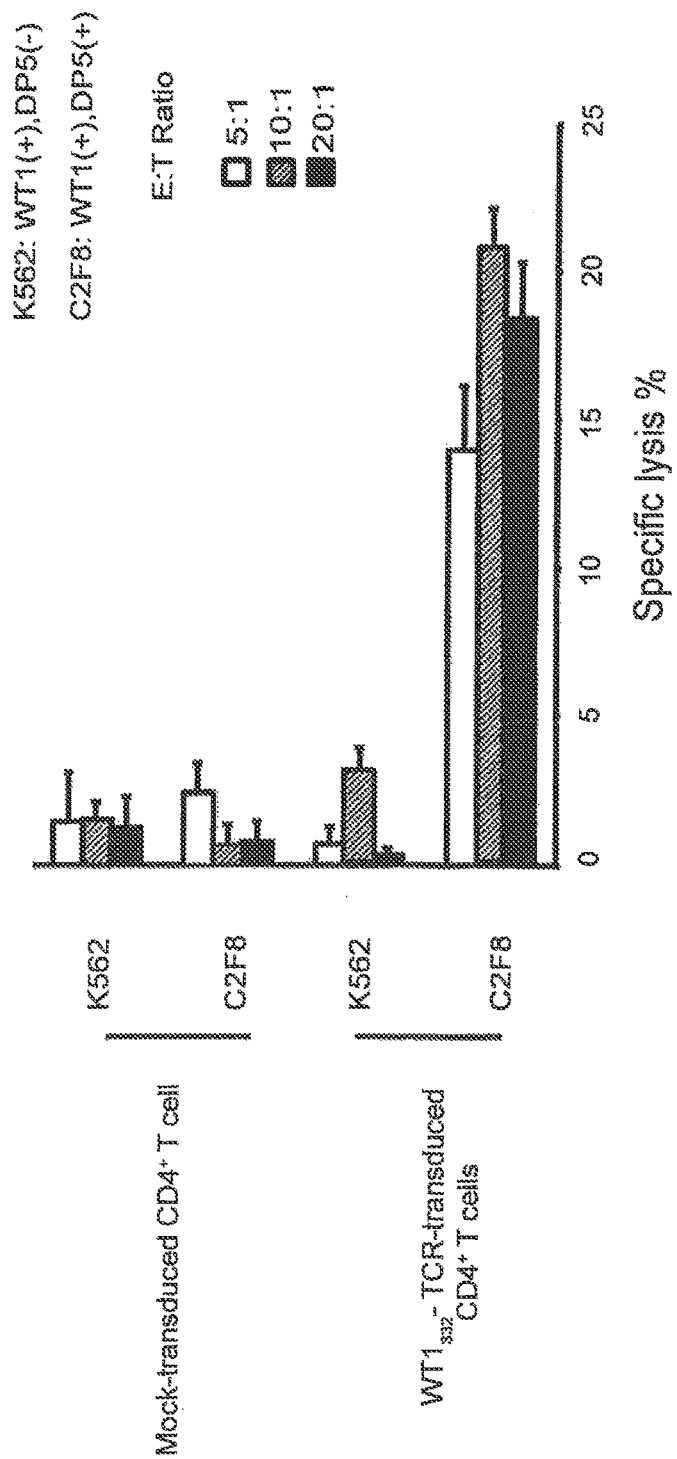
FIG. 4C shows the damage as lysis (%) of K562 cell line and HLA-DPB1*05:01-positive leukemic cell line C2F8 expressing WT1 by WT1$_{332}$-specific CD4$^+$ helper T-cells into which TCR genes have been introduced at the E:T ratio as shown in the figure.

Firstly, HLA-DPB1*05:01 gene was isolated and transfected into leukemia cell line TF-1 expressing WT1 to prepare HLA-DPB1*05:01-positive TF-1 cells. As shown in FIG. 4A, the WT1$_{332}$-TCR-transduced CD4+ T-cells strongly damaged HLA-DPB1*05:01-positive TF-1 cells, however, they did not exhibit cytotoxic activity on HLA-DPB*05:01-negative TF-1 cells. Then, in order to confirm whether this cytotoxic activity is WT1-specific, B-LCL(+) was prepared by overexpressing WT1 gene in HLA-DPB1*05:01-positive B-LCL cells not expressing WT1 (indicated as B-LCL(−)), and these cells were used as target cells to evaluate the cytotoxic activity of WT1$_{332}$-TCR-transduced CD4; T-cells. As shown in FIG. 4B, B-LCL(+) was strongly damaged by the WT1$_{332}$-TCR-transduced CD4+ T-cells, however, B-LCL(−) was not damaged. From these results, it was revealed that the WT1$_{332}$-TCR-transduced CD4+ T-cells had the HLA-DPB1*05:01-restricted and WT1-specific cytotoxic activity. Further, the cytotoxic activity of the WT1$_{332}$-TCR-transduced CD4+ T-cells was confirmed by using leukemia cell line C2F8 which was HLA-DPB*05:01-positive and expressed WT1 (FIG. 4C).

Figure 4D:
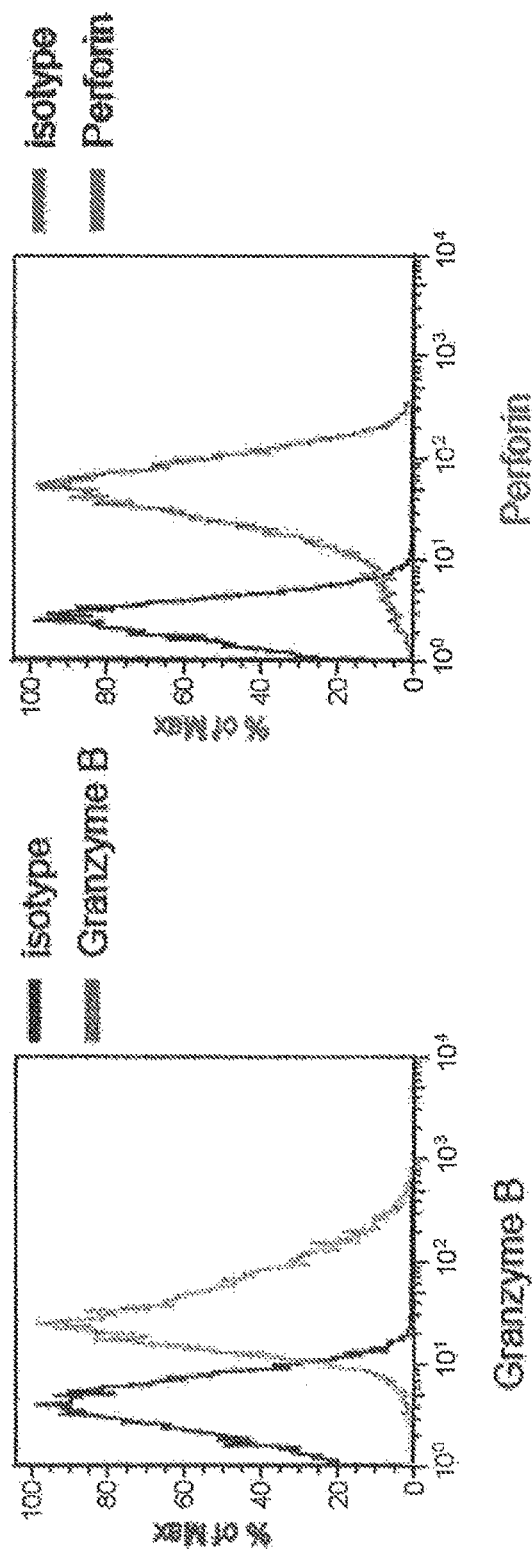
FIG. 4D shows the results by flow-cytometry for the expression of GranzymeB (left) and Perfolin (right) in WT1$_{332}$-specific CD4$^+$ helper T-cells into which TCR genes have been introduced.

Next, it was examined whether WT1$_{332}$-TCR-transduced CD4+ T-cells exerted the cytotoxic activity via the granzyme B and perforin pathway. High expressions of granzyme B and perforin were found in the WT1$_{332}$-TCR-transduced CD4+ T-cells (FIG. 4D).

Figure 4E:
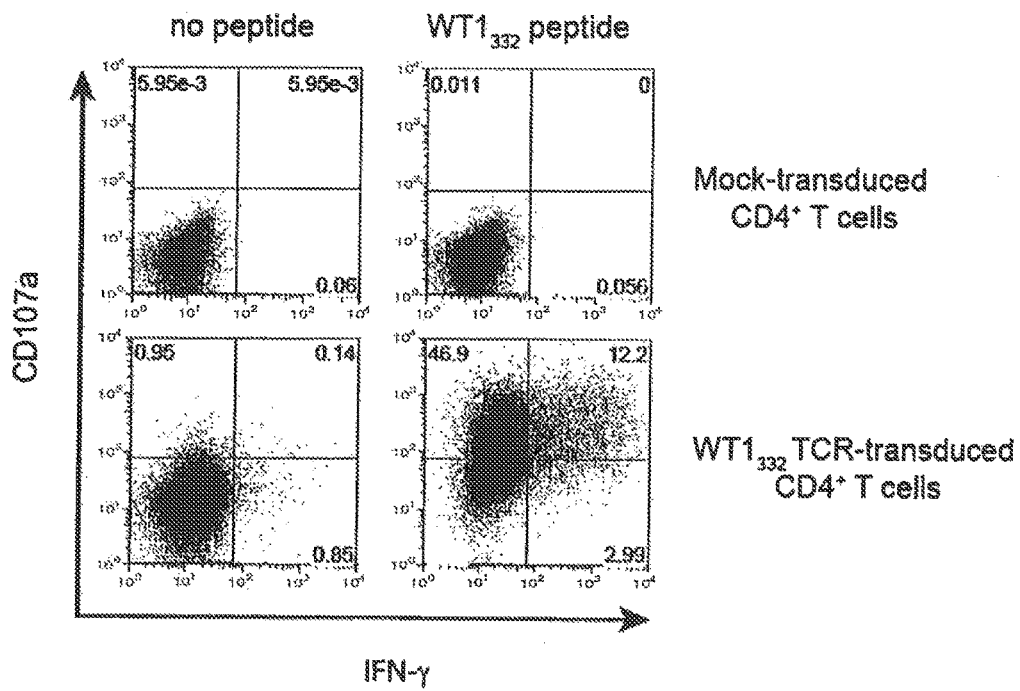
FIG. 4E shows the results by flow-cytometry for the frequency of CD107a producing cells and IFN-γ producing cells of WT1$_{332}$-specific CD4$^+$ helper T-cells into which TCR genes have been introduced, cultured according to the method described in Example 4.

WT1$_{332}$-TCR-transduced CD4+ T-cells and CD4+ T-cells similarly treated with mock-vector (mock-transduced CD4+ T-cells) were cultured with HLA-DPB1*05:01-positive TF-1 cells pulsed with WT1$_{332}$ peptide or HLA-DPB1*05:01-positive TF-1 cells not pulsed with WT1$_{332}$ peptide for 5 hours in the presence of anti-CD107a-APC-monoclonal antibody. Then, IFN-γ-staining was performed and the resultants were subjected to Flow cytometry. The co-expression of IFN-γ and CD107a was found in the WT1$_{332}$-TCR-transduced CD4+ T-cells only when the WT1$_{332}$-TCR-transduced CD4+ T-cells were incubated with HLA-DPB1*05:01-positive TF-1 cells pulsed with WT1$_{332}$ peptide (FIG. 4E). This shows that the degranulation occurs in the WT133$_2$-TCR-transduced CD4+ T-cells.

Figure 4F:
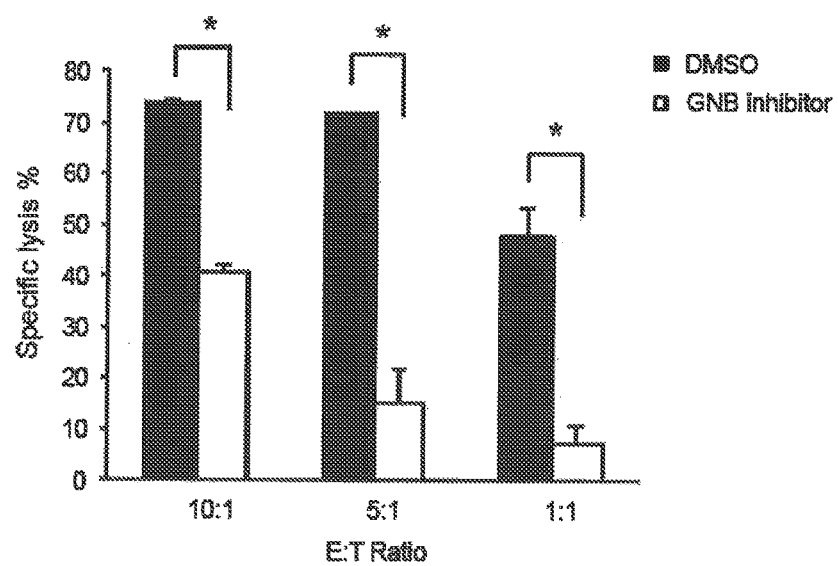
FIG. 4F is a bar graph showing the results for the comparison of the cell damaging activity of WT1$_{332}$-specific CD4$^+$ helper T-cells into which TCR genes have been introduced against HLA-CPB1*05:01-positive TF-1 cells pretreated with Ac-IETD-Cho, with the cell damaging activity of WT1$_{332}$-specific CD4$^+$ helper T-cells into which TCR genes have been introduced against TF-1 cells pretreated with DMSO. Height of bars represents the average value with bars of standard deviation. Asterisk represents $p<0.05$.

To confirm whether the cytotoxic activity of the WT1$_{332}$-TCR-transduced CD4+ T-cells was dependent on the granzyme B/perforin pathway, HLA-DPB1*05:01-positive TF-1 cells pretreated with 100 μM of a granzyme-inhibitor, Ac-IETD-Cho, were used as target cells. The HLA-DPB1*05:01-positive TF-1 cells were pretreated with 100 μM of Ac-IETD-Cho or DMSO (control) for 2 hours, then labeled with $^{51}$Cr, and incubated with WT1$_{332}$-TCR-transduced CD4+ T-cells, and $^{51}$Cr releasing assay was performed. The cytotoxic activity of the WT1$_{332}$-TCR-transduced CD4+ T-cells on HLA-DPB1*05:01-positive TF-1 cells pretreated with Ac-IETD-Cho was markedly lower compared with the cytotoxic activity on TF-1 cells pretreated with DMSO (FIG. 4F).

Considering these results together, it was confirmed that the WT1$_{332}$-TCR-transduced CD4+ T-cells obtained by the present invention directly recognized HLA-DPB1*05:01-

Example 5

Example 5 Anti-Tumor Effect in NOG® Mouse by Human CD4+ T-Cells Transduced with TCR Genes Derived from WT1$_{332}$-Specific CD4+ T-Cells WT1-expressing HLA-DPB1*05:01-positive human leukemia cells C2F8 (5×10⁴ cells) were transferred to NOG® mice (7 mice) via tail vein. Next day, as an experimental group, human CD4+ T-cells transduced with HLA-DPB1*05:01-restricted WT1$_{332}$-specific TCR genes (SEQ ID Nos: 14 and 15) (5×10⁶ cells) and T-cell-depleted human peripheral blood mononuclear cells (2×10⁶ cells) from the same subject as antigen-presenting cells were transferred to the above NOG® mice (3 mice). As a control, human CD4+ T-cells transduced with the control vector (5×10⁶ cells) and T-cell-depleted human peripheral blood mononuclear cells (2×10⁶ cells) from the same subject as antigen-presenting cells were transferred to the above NOG® mice (4 mice).

After 1 and 2 weeks, human CD4+ T-cells transduced with HLA-DPB1*05:01-restricted WT1$_{332}$-specific TCR genes (5×10⁶ cells) were transferred to the mice of the experimental group via tail vein. Human CD4+ T-cells transduced with control vector (5×10⁶ cells) were transferred to the control mice via tail vein. Then, the survival of mice was examined.

Figure 5:
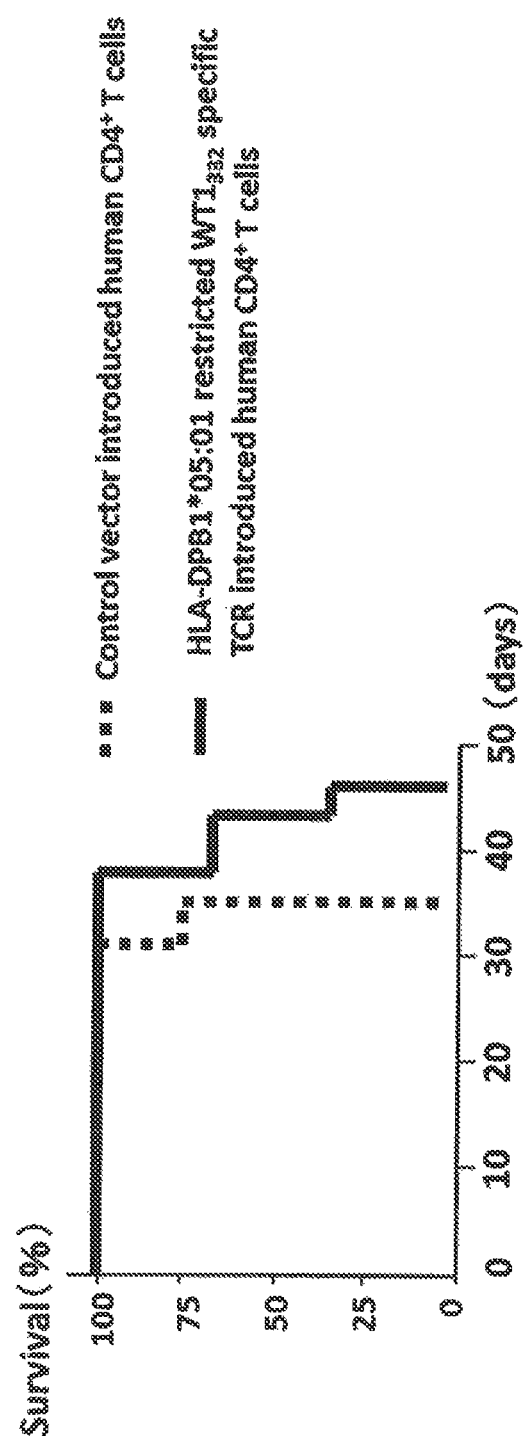
FIG. 5 shows survival curves showing anti-tumor activity in NOG (Registered Trade Mark) mice by human CD4$^+$ T-cells into which TCR genes from WT1$_{332}$-specific CD4$^+$ T-cells have been introduced. The solid line represents the survival curve of mice into which human CD4$^+$ T-cells have been transferred, into which HLA-DPB1*05:01 restricted WT1$_{332}$-specific TCR have been introduced. The broken line represents the survival curve of mice into which human CD4$^+$ T-cells have been transferred, into which a control vector have been introduced.

The results are shown in FIG. 5. Since the survival rate of the mice of the experimental group exceeded the survival rate of the mice of control, it was shown that HLA-DPB1*05:01-restricted WT1$_{332}$-specific TCR-transduced human CD4+ T-cells had an anti-tumor effect in vivo.

INDUSTRIAL APPLICABILITY

The present invention can be used in the fields of pharmaceuticals for treating or preventing cancer, of reagents for cancer research, and of cancer test kits or reagents, and the like.

The invention claimed is:

1. A method for the treatment of a WT1-expressing cancer in a subject, comprising introducing a CD4+ helper T-cell into the subject,
wherein the CD4+ helper T cell is obtained by introducing a TCR gene into a CD4+ T cell, wherein
(i) the TCR gene comprises a pair of polynucleotides chosen from:
   (a) SEQ ID NO: 1 and SEQ ID NO: 2;
   (b) SEQ ID NO: 3 and SEQ ID NO: 4;
   (c) SEQ ID NO: 5 and SEQ ID NO: 6;
   (d) SEQ ID NO: 3 and SEQ ID NO: 7;
   (e) SEQ ID NO: 8 and SEQ ID NO: 9;
   (f) SEQ ID NO: 10 and SEQ ID NO: 12;
   (g) SEQ ID NO: 11 and SEQ ID NO: 12;
   (h) SEQ ID NO: 13 and SEQ ID NO: 15,
   (i) SEQ ID NO: 14 and SEQ ID NO: 15;
   (j) SEQ ID NO: 16 and SEQ ID NO: 17;
   (k) SEQ ID NO: 18 and SEQ ID NO: 19;
   (l) SEQ ID NO: 20 and SEQ ID NO: 21;
   (m) SEQ ID NO: 22 and SEQ ID NO: 24;
   (n) SEQ ID NO: 23 and SEQ ID NO: 24;
   (o) SEQ ID NO: 25 and SEQ ID NO: 26;
   (p) SEQ ID NO: 27 and SEQ ID NO: 4;
   (q) SEQ ID NO: 28 and SEQ ID NO: 29;
   (r) SEQ ID NO: 30 and SEQ ID NO: 32;
   (s) SEQ ID NO: 31 and SEQ ID NO: 32;
   (t) SEQ ID NO: 33 and SEQ ID NO: 34;
   (u) SEQ ID NO: 35 and SEQ ID NO: 36;
   (v) SEQ ID NO: 37 and SEQ ID NO: 38;
   (w) SEQ ID NO: 39 and SEQ ID NO: 40;
   (x) SEQ ID NO: 41 and SEQ ID NO: 42;
   (y) SEQ ID NO: 43 and SEQ ID NO: 44;
   (z) SEQ ID NO: 45 and SEQ ID NO: 46;
   (aa) SEQ ID NO: 47 and SEQ ID NO: 48;
   (bb) SEQ ID NO: 49 and SEQ ID NO: 50;
   (cc) SEQ ID NO: 51 and SEQ ID NO: 52;
   (dd) SEQ ID NO: 53 and SEQ ID NO: 54;
   (ee) SEQ ID NO: 55 and SEQ ID NO: 57;
   (ff) SEQ ID NO: 56 and SEQ ID NO: 57; and
   (gg) SEQ ID NO: 58 and SEQ ID NO: 59; or
(ii) the TCR gene comprises a pair of polynucleotides that are complementary to or degenerate of any of the pairs of polynucleotides listed in (i).

* * * * *